(12) United States Patent
Massad

(10) Patent No.: US 7,717,858 B2
(45) Date of Patent: May 18, 2010

(54) INTERVENTIVE-DIAGNOSTIC DEVICE

(75) Inventor: Tamir Massad, Moshav Ben-Shemen (IL)

(73) Assignee: Intercure Ltd., Neve-Ilan (IL)

( * ) Notice: Subject to any disclaimer, the term of this patent is extended or adjusted under 35 U.S.C. 154(b) by 1623 days.

(21) Appl. No.: 10/685,956

(22) Filed: Oct. 15, 2003

(65) Prior Publication Data

US 2004/0077934 A1    Apr. 22, 2004

Related U.S. Application Data

(62) Division of application No. 09/611,304, filed on Jul. 6, 2000, now Pat. No. 6,662,032.

(30) Foreign Application Priority Data

Jul. 6, 1999  (IL) .................................. 130818

(51) Int. Cl.
*A61B 5/08* (2006.01)
*G01G 23/01* (2006.01)
*H01G 7/00* (2006.01)
*H01G 5/01* (2006.01)

(52) U.S. Cl. .................. 600/535; 600/534; 73/1.08; 73/1.15; 361/277; 361/278

(58) Field of Classification Search .............. 600/534, 600/535; 73/1.15, 780; 324/345–364
See application file for complete search history.

(56) References Cited

U.S. PATENT DOCUMENTS

| | | | |
|---|---|---|---|
| 4,033,332 A * | 7/1977 | Hardway et al. ............ 600/535 |
| 4,102,332 A | 7/1978 | Gessman ................. 128/2.1 A |
| 4,195,626 A | 4/1980 | Schweizer ................... 128/774 |
| 4,381,788 A | 5/1983 | Douglas ..................... 128/722 |
| 4,474,185 A | 10/1984 | Diamond .................... 128/722 |
| 4,526,078 A | 7/1985 | Chadabe ..................... 84/1.03 |
| 4,580,574 A | 4/1986 | Gavish ....................... 128/660 |
| 4,672,849 A * | 6/1987 | Hoshino ...................... 73/579 |
| 4,798,538 A | 1/1989 | Yagi ........................... 434/262 |
| 4,827,943 A | 5/1989 | Bornn et al. ................ 600/481 |
| 4,883,067 A | 11/1989 | Knispel et al. ............. 128/732 |
| 5,052,400 A | 10/1991 | Dietz ......................... 128/722 |
| 5,070,321 A | 12/1991 | Einhorn et al. ............. 340/608 |
| 5,076,281 A | 12/1991 | Gavish ....................... 128/721 |
| 5,131,399 A * | 7/1992 | Sciarra ....................... 600/484 |
| 5,267,942 A | 12/1993 | Saperston .................... 600/28 |
| 5,329,931 A | 7/1994 | Clauson et al. ............ 600/529 |
| 5,367,292 A | 11/1994 | Szoke et al. ............... 340/608 |
| 5,423,328 A | 6/1995 | Gavish ....................... 128/721 |
| 5,485,850 A | 1/1996 | Dietz ......................... 128/716 |
| 5,564,429 A | 10/1996 | Worth et al. | |
| 5,577,510 A | 11/1996 | Chittum et al. | |
| 5,590,282 A | 12/1996 | Clynes .................. 395/200.02 |
| 5,596,994 A | 1/1997 | Bro ............................ 128/732 |
| 5,678,571 A | 10/1997 | Brown ....................... 128/898 |

(Continued)

*Primary Examiner*—Charles A Marmor, II
*Assistant Examiner*—Christian Y Jang
(74) *Attorney, Agent, or Firm*—Ladas and Parry LLP

(57) ABSTRACT

Apparatus for improving health of a user is provided, including a first sensor, adapted to measure a first physiological variable, which is indicative of a voluntary action of the user. A second sensor is adapted to measure a second physiological variable, which is substantially governed by an autonomic nervous system of the user. Circuitry is adapted to receive respective first and second sensor signals from the first and second sensors, and, responsive thereto, to generate an output signal which directs the user to modify a parameter of the voluntary action.

6 Claims, 16 Drawing Sheets

U.S. PATENT DOCUMENTS

| | | | |
|---|---|---|---|
| 5,690,691 A | 11/1997 | Chen et al. | 607/40 |
| 5,752,509 A | 5/1998 | Lachmann et al. | 128/204.23 |
| 5,782,878 A | 7/1998 | Morgan | 607/5 |
| 5,794,615 A | 8/1998 | Estes | 128/204.23 |
| 5,800,337 A | 9/1998 | Gavish | 600/27 |
| 5,827,179 A | 10/1998 | Lichter et al. | 600/300 |
| 6,001,065 A | 12/1999 | De Vito | 600/544 |
| 6,047,203 A | 4/2000 | Sackner et al. | 600/388 |
| 6,050,940 A | 4/2000 | Braun et al. | 600/300 |
| 6,090,037 A | 7/2000 | Gavish | 600/27 |

\* cited by examiner

INTERVENTIVE-DIAGNOSTIC DEVICE

This application is a divisional of application Ser. No. 09/611,304 filed on Jul. 6, 2000 now U.S. Pat. No. 6,662,032, claims the benefit thereof and incorporates the same by references.

FIELD OF THE INVENTION

The present invention relates generally to medical devices, and specifically to treatment and diagnostic devices which provide feedback to a user regarding a physiological variable of the user.

BACKGROUND OF THE INVENTION

Devices which measure a physiological variable of a user and which then provide feedback to the user for the purpose of modifying the variable are well known in the art. U.S. Pat. No. 5,076,281, and U.S. Pat. No. 5,800,337, to the present inventor, which are incorporated herein by reference, both describe methods and devices for modifying biorhythmic activity by measuring one or more variables of a user. The patents describe the generation of a stimulus which is provided to the user, so as to change the biorhythmic activity of the user in a way that is related to the monitored biorhythmic activity.

U.S. Pat. No. 5,423,328, to the present inventor, which is also incorporated herein by reference, describes a stress-detecting device for monitoring respiration, and, in particular, a method for detecting and monitoring circumferential changes in the chest or abdomen of a user resulting from breathing. U.S. Pat. No. 4,580,574, to the present inventor, which is also incorporated herein by reference, describes a method for non-invasively monitoring properties of living tissue.

An abstract entitled, "Repeated blood pressure measurements may probe directly an arterial property," *American Journal of Hypertension* (April, 2000); 13(4), part 2: 190A, by B. Gavish, which is incorporated herein by reference, proposes that the slope of a line relating multiple systolic and diastolic blood pressure measurements is a physiologically-meaningful parameter.

An article entitled, "Challenges facing 3-D audio display design for multimedia," *Journal of the Acoustical Society of America* (1999); J 105:1357, by D. R. Begault, which is incorporated herein by reference, describes the production and psychophysiological implications of 3-D sound, which enables listeners to perceive the direction of a sound source in three dimensions. Another article, entitled, "Localization using nonindividualized head-related transfer functions," by Wenzel et al., *Journal of the Acoustical Society of America* (July, 1993); 94(1), pp. 222-234, which is incorporated herein by reference, describes the synthesis of 3-D sound, so as to enable listeners to perceive the 3-D direction and localization of a virtual sound source. In addition, a cassette distributed by NASA/Ames Research Center, entitled, "Demonstration of 3-D auditory display," allows a listener using a normal cassette player and standard earphones to experience the three-dimensional effect.

Other articles of interest include:

(a) an article by Cooke et al., entitled, "Controlled breathing protocols probe human autonomic cardiovascular rhythms," *American Journal of Physiology*, (1998); 274: H709-H718, (b) an article by Pitzalis et al., entitled, "Effect of respiratory rate on the relationship between RR interval and systolic blood pressure fluctuations: a frequency-dependent phenomenon," *Cardiovascular Research* (1998); 38:332-339, (c) an article by Bernardi et al., entitled, "Effect of breathing rate on oxygen saturation and exercise performance in chronic heart failure," *The Lancet* (May 2, 1998); 351:1308-1311, (d) an article by Mortara et al., entitled, "Abnormal awake respiratory patterns are common in chronic heart failure and may prevent evaluation of autonomic tone by measures of heart rate variability," *Circulation* (Jul. 1, 1997); 96:246-252, (e) an article by La Rovere et al., entitled, "Baroreflex sensitivity and heart-rate variability in prediction of total cardiac mortality after myocardial infarction," *The Lancet* (Feb. 14, 1998); 351:478-484, and (f) an article by Gimondo and Mirk, entitled, "A new method for evaluating small intestinal motility using duplex Doppler sonography," *AJR American Journal of Roentgenology* (January, 1997); 168(1):187-192.

All of these articles are incorporated herein by reference.

Devices which are at least partially operated remotely are also known in the art. U.S. Pat. No. 4,102,332, to Gessman, which is incorporated herein by reference, describes a device for remote telephonic resuscitation. The device includes an electrocardiograph and a defibrillator which are carried by a user with a known history of cardiac symptoms, and which may be used to diagnose and treat acute cardiac symptoms. In order to facilitate the diagnosis and treatment, the device may be connected to a telephone line, so that a remote physician may make the diagnosis and perform the treatment.

U.S. Pat. No. 4,195,626, to Schweizer, which is incorporated herein by reference, describes a biofeedback chamber for applying audible, visual electrical or tactile stimuli to a subject according to a rhythmic pattern. The subject's reactions are measured, analyzed and used to control the stimuli.

U.S. Pat. No. 5,782,878, to Morgan, which is incorporated herein by reference, describes a system including an external defibrillator, a defibrillator communicator, and a communication network. In order to perform a defibrillation, information is transmitted back and forth between a patient and a communication station.

U.S. Pat. No. 5,794,615, to Estes, which is incorporated herein by reference, describes a system for treatment of congestive heart failure. The patent describes controlling the flow rate of a pressurized gas delivered to a patient during the two phases of the respiratory cycle independently. The system may be fully automated responsive to feedback provided by a flow sensor that determines the estimated patient flow rate.

U.S. Pat. No. 5,678,571, to Brown, which is incorporated herein by reference, describes a method for treating a medical condition in a patient comprising choosing a psychological strategy for treating the medical condition, and then encoding electronic instructions for an interactive video game. The game implements the psychological strategy, and loads the electronic instructions into a microprocessor-based unit equipped with a display for displaying the video game. The game contains scoring instructions to quantitatively analyze the medical condition of the patient, counseling instructions and self-care instructions. The video game can be used in conjunction with a physiological variable measuring device connected to the microprocessor-based unit.

U.S. Pat. No. 5,752,509, to Lachmann, et al. describes a system for artificially ventilating a patient. The ventilation system has a gas delivery unit for delivering controllable inspiration pulses to a patient, a monitoring unit for measuring at least one parameter related to the function of the circulatory system, such as a blood gas analyzer, and a control unit for determining an optimal peak inspiratory pressure and pressure amplitude for the inspiration pulse, based on the measured circulatory system parameter.

Descriptions of respiratory monitoring apparatus which assess capacitance are found in U.S. Pat. Nos. 5,485,850 to Dietz, 4,033,332 to Hardway et al., 4,381,788 to Douglas, 4,474,185 to Diamond, and in U.S. Pat. Nos. 5,367,292, 5,070,321, and 5,052,400, all of which are incorporated herein by reference.

U.S. Pat. No. 5,690,691 to Chen, et al., which is incorporated herein by reference, describes a portable or implantable gastric pacemaker, which includes multiple electrodes that are positioned on an organ in the gastrointestinal (GI) tract, so as to deliver electrical stimulation to pace the peristaltic movement of material through the GI tract.

U.S. Pat. Nos. 5,590,282 and 4,526,078, which are incorporated herein by reference, describe techniques for causing a computer to compose music.

U.S. Pat. No. 4,883,067 to Knispel et al., which is incorporated herein by reference, describes a method for translating a subject's electroencephalogram into music, so as to induce and control various psychological and physiological states of the subject.

U.S. Pat. No. 4,798,538 to Yagi, which is incorporated herein by reference, describes an abdominal respiration training system. The state of the abdominal respiration of a person is measured by a sensor attached to the abdominal region, and the detected breath pattern is compared with an ideal breath pattern.

SUMMARY OF THE INVENTION

It is an object of some aspects of the present invention to provide methods and apparatus which enable a user to improve a physiological variable of the user.

It is a further object of some aspects of the present invention to provide methods and apparatus which convey a stimulus to a user so as to improve a physiological variable of the user.

It is yet a further object of some aspects of the present invention to provide remotely-mediated methods and apparatus which enable a user to improve a physiological variable of the user.

It is an additional object of some aspects of the present invention to provide remotely-mediated methods and apparatus which enable a user to modify physiological variables to improve health or manage a specific disease.

In preferred embodiments of the present invention, an interventive-diagnostic system comprises a local computing device at a local site, which applies an intervention to a user at the site and receives one or more input signals from one or more sensors attached to the user. The input signals are indicative of a physiological condition of the user. The local device makes a preliminary analysis of the input signals, thereby generating a set of analyzed data, and typically modifies a subsequent intervention responsive to the analyzed data. The set of analyzed data and/or some or all of the input signals are transmitted as data to a remote facility for further analysis. The remote facility comprises a program operator, optionally using a computer. The program operator makes a further analysis of the data received, and transmits a result of the analysis back to the local device and/or to the user. The local device uses the result from the remote facility and the input signals to modify a subsequent intervention which is applied to the user.

Preferably, the input signals and the analysis thereof made by the local device are stored by the device in a data logger, typically comprising an electronic memory and/or a permanent storage medium. Some or all of the contents of the data logger are preferably transmitted intermittently, on-line, to the remote facility for processing. Typically, the stored data are utilized in combination with the input signals to generate the preliminary analysis. Additionally, by examining data stored in the data logger from several sessions, trends can be calculated by the device or at the remote facility to evaluate the success of a particular intervention strategy. Subsequently, either on-line or off-line, the intervention strategy may be changed responsive to the evaluation.

Typically, the further analysis performed by the program operator comprises activities which would be difficult or impossible to perform at the local site. The result of the analysis may comprise a direct response to the user, or a communication between computing devices. For example, the program operator may provide help to the user for operating the local device. Alternatively, the program operator and/or the computer at the remote facility may transmit the result directly to the local device, for example, in order to change a characteristic, setting or operational mode of the device. For some applications, a human program operator is not necessary, and the computer at the remote facility automatically performs the analysis.

An "intervention" is to be understood in the disclosure and in the claims as a generation of a stimulus intended to modify one or more physiological variables of a user. For example, the intervention transmitted to the user may comprise an intelligible input stimulus, such as a sound pattern and/or dynamic graphical pattern, which is generated according to one or more predefined programs resident within the local device. The stimulus is typically intended to modify breathing of the user, for example, by training the user to initiate a new breathing pattern. Most preferably, the intervention is one which is known to have a positive effect on aspects of one or more of the user's physiological systems, such as the cardiovascular, pulmonary, and/or neurological systems.

The local device and/or the remote facility are also able to generate a "diagnosis" responsive to a physiological variable of the user. A diagnosis is to be understood in the disclosure and in the claims as the generation of an evaluation responsive to one or more physiological variables of the user, which evaluation may be monitored without modifying the physiological variables.

The combination of a local device and a remote facility operating together to provide intervention and diagnosis significantly enhances the ability of the local device to generate an intervention which benefits the user. Furthermore, the combination enables the remote facility to follow effects, such as changes in diagnosis, generated by the intervention and to interact with the local device and/or the user in order to give appropriate further feedback as appropriate.

Wellness and disease-management programs are one of the goals of modern healthcare systems. These are addressed in preferred embodiments of the present invention, in which the interventive-diagnostic system is operated over an extended period of time, on the order of months, and progress of the user is followed by the remote facility during the period. Most preferably, a plurality of programs are stored within the local computing device, which programs comprise a sequence of modes of device operation which are followed by the user during the period. During the extended period, the remote facility monitors that the user is correctly adhering to a particular program, provides help as appropriate, and obtains data relating to the user's progress.

In some preferred embodiments of the present invention, the stimulus provided to the user is in the form of a game, and the parameters of the game are altered so that playing the game induces the user to modify the physiological variable. Having a stimulus in the form of a game, most preferably an audiovisual game, encourages users who are children to actively participate in a therapeutic intervention process. For example, children with pulmonary or motor-related neurological disease, such as asthma or hyperactivity, may be benefited by use of these embodiments of the invention.

In some preferred embodiments of the present invention, the local device is provided to the user from the remote facility, or from some other facility, for an evaluation period, during which period the user operates the system as described above. On completion of the evaluation period, the user is able to return the device to one of the facilities, or continue to use the device after a payment has been received by one of the facilities. Alternatively or additionally, the local device is given at no charge to a receiver, and is enabled to exchange data with the remote operator, as described hereinabove, responsive to regular payments to the remote facility.

There is therefore provided, in accordance with a preferred embodiment of the present invention, a method for inducing a modification of a physiological variable of a user, including:

applying an intervention via a device to the user responsive to a set of one or more intervention parameters;

measuring a physiological variable responsive to the intervention;

transmitting a signal responsive to the physiological variable to a remote facility for processing;

receiving a reply from the remote facility responsive to the signal; and applying the intervention via the device to the user responsive to the reply.

Preferably, the physiological variable is a variable representative of a biorhythmic activity of the user, and is changed as a direct consequence of the intervention. Further preferably, the intervention includes instructing the user to voluntarily change the physiological variable, directly or indirectly, for example, by modifying a parameter of the user's breathing, or by affecting blood flow responsive to respiration and/or respiratory movements.

Preferably, transmitting the signal includes connecting the device to the remote facility via a distributed network or via a direct communication link.

In a preferred embodiment, the device and the remote facility include respective industry-standard computers, operating respective programs.

Preferably, applying the intervention includes providing an intelligible sensory stimulus to the user.

Further preferably, transmitting the signal and receiving the reply include communicating a verbal message or transmitting and/or receiving a set of data.

Still further preferably, the device includes a comparator which compares a current physiological state of the user to a previous physiological state of the user, in order to determine a change in the physiological state responsive to the intervention.

Still further preferably, measuring the physiological variable includes generating a diagnosis and modifying the set of one or more intervention parameters responsive to the diagnosis.

In a preferred embodiment, the intervention includes a routine intervention, applied to the user at generally regular intervals, for example, in a non-emergency setting.

There is also provided, in accordance with a preferred embodiment of the present invention, a method for inducing a modification of a physiological variable of a user, including:

providing an electronic game having a game parameter, the game to be played by the user;

applying an intervention via the game to the user responsive to the game parameter;

measuring a physiological variable responsive to the intervention; and modifying the game parameter responsive to the measured physiological variable.

Preferably, providing the electronic game includes:

connecting the game to a remote facility;

transmitting the game parameter to the remote facility, and transmitting the physiological variable to the remote facility.

In a preferred embodiment, connecting the game to the remote facility includes receiving a response from the remote facility for the purpose of modifying the game parameter. Alternatively or additionally, another user operates the method at the remote facility.

Preferably, the physiological variable is changed as an indirect consequence of the intervention. In a preferred embodiment, the physiological variable includes an indication of blood oxygenation, cardiac electrical state, respiration or blood pressure.

In a preferred embodiment, the user has congestive heart failure, asthma, chronic obstructive pulmonary disease, hypertension, or cystic fibrosis. Alternatively, the user is generally healthy, and uses aspects of the present invention in order to obtain psychological stress-relief and/or relaxation, or for purposes of muscle re-education, athletic training, or entertainment. For some applications, measuring the physiological variable includes receiving a sound responsive to respiratory activity, such as wheezing.

Alternatively or additionally, measuring the physiological variable includes receiving an indication of microvascular blood flow and/or of the stiffness of at least one blood vessel.

There is further provided, in accordance with a preferred embodiment of the present invention, a method for modifying a physiological variable of a user, including:

providing the user with an interventional device capable of modifying the variable responsive to an input from a remote facility;

enabling the device to operate during a time-limited period; and enabling the device to operate after the time-limited period, responsive to a receipt of payment.

Preferably, providing the user with the interventional device includes facilitating the user and the remote facility to enter into an agreement regarding operation of the device. Typically, the receipt of payment includes a transfer of funds to the remote facility.

There is still further provided, in accordance with a preferred embodiment of the present invention, a method for enabling an intervention, including:

receiving a signal corresponding to a measured physiological variable of a remote user, the physiological variable having been measured responsive to a first intervention via a device; and transmitting a reply responsive to the signal, to modify aspects of a second intervention applied via the device.

Preferably, receiving the signal includes generating a diagnosis responsive to the measured physiological variable of the remote user.

There is additionally provided, in accordance with a preferred embodiment of the present invention, apparatus for inducing a modification of a physiological variable of a user, including:

a sensor, which generates a measure of the physiological variable of the user;

a stimulation unit, which provides an intervention to the user; and a device, which is coupled to the sensor and the stimulation unit, and which:

determines a set of one or more intervention parameters responsive to the measure of the physiological variable;

operates the stimulation unit responsive to the set of one or more intervention parameters;

transmits a signal responsive to the physiological variable to a remote facility for processing;

receives a reply from the remote facility responsive to the signal; and applies the intervention via the stimulation unit to the user responsive to the reply.

Preferably, the device includes a comparator and a memory, wherein an indication of a physiological state of the user is intermittently stored in the memory, and wherein the comparator compares a current indication of the physiological state to a previous indication of the physiological state, in order to determine a change in the user's physiological state.

In a preferred embodiment, the stimulation unit includes an industry-standard computer.

There is yet additionally provided, in accordance with a preferred embodiment of the present invention, apparatus for inducing a modification of a physiological variable of a user, including:

an electronic game to be played by the user, the game applying an intervention to the user responsive to a game parameter;

a sensor, which measures a physiological variable responsive to playing of the game; and a processor which modifies the game parameter responsive to the measured physiological variable.

Preferably, the processor is located at a remote facility. In a preferred embodiment, another user plays a similar game at the remote facility.

There is also provided, in accordance with a preferred embodiment of the present invention, apparatus for enabling an intervention, including:

a receiver, located at a local facility, which receives a signal corresponding to a measured physiological variable of a remote user, the physiological variable having been measured responsive to a first intervention via a device; and a transmitter, located at the local facility, which transmits a reply responsive to the signal, to modify aspects of a subsequent intervention applied via the device.

There is also provided, in accordance with a preferred embodiment of the present invention, a method for generating music, including:

receiving a rhythm signal corresponding to a rhythm of a cyclic physiological activity of a user, the physiological activity having first and second activity phases thereof;

analyzing the rhythm signal to determine first and second durations thereof, respectively corresponding to the first and second activity phases;

determining first and second new durations responsive to desired changes of the first and second durations of the rhythm signal;

generating responsive to the new durations a music signal for presentation to the user, the music signal having first and second music phases thereof respectively corresponding to the first and second activity phases, a duration of each of the music phases expressible as being approximately equal to an integer multiple of a base duration, the integer multiple being less than or equal to four; and directing the user to modify durations of the first and second activity phases responsive to the respective durations of the first and second music phases.

Alternatively or additionally, generating the music signal includes setting the duration of one of the music phases to be approximately equal to an integer multiple of the other one of the music phases.

Alternatively or additionally, directing the user to modify the durations includes directing the user to attempt to perform the first and second activity phases of the physiological activity such that the respective durations thereof are substantially equal to the durations of the first and second music phases.

Alternatively or additionally, receiving the rhythm signal includes receiving a motion signal corresponding to an activity of the user selected from the list consisting of: walking, jogging, and running.

Alternatively or additionally, receiving the rhythm signal includes receiving a respiration signal corresponding to respiration of the user.

Alternatively or additionally, receiving the breathing signal includes receiving an indication of a timing characteristic of inspiratory and expiratory phases of the respiration.

Alternatively or additionally, determining the new durations includes determining the new durations responsive to a vasomotor frequency of the user.

Alternatively or additionally, the method includes measuring a cardiovascular variable of the user and determining the vasomotor frequency responsive thereto.

There is also provided, in accordance with a preferred embodiment of the present invention, a method for generating music, including:

receiving a rhythm signal corresponding to a rhythm of a cyclic physiological activity of a user, the physiological activity having first and second activity phases thereof;

analyzing the rhythm signal to determine first and second durations thereof, respectively corresponding to the first and second activity phases;

determining first and second new durations responsive to desired changes of the first and second durations of the rhythm signal;

generating responsive to the new durations a music signal for presentation to the user, the music signal having first and second music phases thereof respectively corresponding to the first and second activity phases, a duration of one of the music phases being approximately equal to an integer multiple of a duration of the other one of the music phases; and directing the user to modify durations of the first and second activity phases responsive to the respective durations of the first and second music phases.

Alternatively or additionally, directing the user to modify the durations includes directing the user to attempt to perform the first and second activity phases of the physiological activity such that the respective durations thereof are substantially equal to the durations of the first and second music phases.

Alternatively or additionally, receiving the rhythm signal includes receiving a respiration signal corresponding to respiration of the user.

Alternatively or additionally, determining the new durations includes determining the new durations responsive to a vasomotor frequency of the user.

Alternatively or additionally, the method includes measuring a cardiovascular variable of the user and determining the vasomotor frequency responsive thereto.

There is also provided, in accordance with a preferred embodiment of the present invention, a method for generating music, including:

receiving a rhythmic physiological pattern corresponding to a rhythm of a physiological activity of a user;

analyzing the rhythmic physiological pattern to determine an actual activity pattern thereof;

determining a new activity pattern responsive to a desired change of the actual activity pattern;

generating a music signal for presentation to the user, the music signal having two or more sets of notes, at least one of the sets of notes having a rhythmic characteristic corresponding to the new activity pattern; and directing the user to modify the rhythm of the physiological activity responsive to the music signal.

Alternatively or additionally, directing the user includes directing the user to modify the rhythm of the physiological activity to correspond to the rhythmic characteristic.

Alternatively or additionally, directing the user includes playing at least part of the music signal.

Alternatively or additionally, directing the user includes outputting a vocal message.

Alternatively or additionally, receiving the rhythmic physiological pattern includes receiving a motion signal corresponding to an activity of the user selected from the list consisting of: walking, jogging, and running.

Alternatively or additionally, generating the music signal includes varying a characteristic of the notes in one of the sets responsive to at least one of: the actual activity pattern and the new activity pattern.

Alternatively or additionally, varying the characteristic includes varying a characteristic of an envelope parameter of the notes.

Alternatively or additionally, generating the music signal includes generating the signal in accordance with the Musical Instrument Digital Interface (MIDI) standard.

Alternatively or additionally, generating the music signal includes defining at least two of the sets of notes as being in distinct layers.

Alternatively or additionally, receiving the rhythmic physiological pattern includes receiving a respiration signal corresponding to respiration of the user.

Alternatively or additionally, receiving the breathing signal includes receiving an indication of a timing characteristic of inspiratory and expiratory phases of the respiration.

Alternatively or additionally, determining the new activity pattern includes determining the new activity pattern responsive to a vasomotor frequency of the user.

Alternatively or additionally, the method includes measuring a cardiovascular variable of the user and determining the vasomotor frequency responsive thereto.

Alternatively or additionally, generating the music signal includes:

substantially not outputting the notes in at least one of the sets when the new activity pattern is characterized by a first rate; and outputting the notes in the at least one of the sets when the new activity pattern is characterized by a second rate, which is slower than the first rate.

Alternatively or additionally, generating the music signal includes:

substantially not outputting the notes in a second one of the sets when the new activity pattern is characterized by the second rate; and outputting the notes in the second set when the new activity pattern is characterized by a third rate, which is slower than the second rate.

Alternatively or additionally, generating the music signal includes substantially not outputting the notes in the at least one of the sets when the new activity pattern is characterized by the third rate.

There is also provided, in accordance with a preferred embodiment of the present invention, a method for generating music, including:

receiving a rhythm signal corresponding to a rhythm of a cyclic physiological activity of a user;

analyzing the rhythm signal to determine a pattern thereof;

determining a new pattern responsive to a desired change of the pattern of the rhythm signal;

generating, responsive to the new pattern, a music signal for presentation to the user;

determining, responsive to a characteristic of the new pattern, a set of music layers to include in the music signal, the layers having notes, such that the notes of one of the layers are played at a generally faster rate than the notes of another one of the layers; and directing the user to modify the rhythm of the physiological activity responsive to the music signal.

Alternatively or additionally, analyzing the rhythm signal to determine the pattern thereof includes analyzing the rhythm signal to determine a characteristic frequency thereof, and determining the new pattern includes determining a new frequency responsive to a desired change of the frequency of the rhythm signal.

Alternatively or additionally, receiving the rhythm signal includes receiving a respiration signal corresponding to respiration of the user.

There is also provided, in accordance with a preferred embodiment of the present invention, apparatus for facilitating improving health of a user, including:

a first sensor, adapted to measure a first physiological variable, which is indicative of a voluntary action of the user;

a second sensor, adapted to measure a second physiological variable, which is not entirely under the direct voluntary control of the user; and circuitry, adapted to receive respective first and second sensor signals from the first and second sensors, and, responsive thereto, to generate an output signal which directs the user to modify a parameter of the voluntary action.

Alternatively or additionally, the circuitry is adapted to generate the output signal such that if the user modifies a parameter of the voluntary action responsive to the output signal, then the second physiological variable will be changed in a desired manner.

Alternatively or additionally, the circuitry is adapted to: (a) generate the output signal to direct the user to modify the parameter of the voluntary action, (b) identify an aspect of the first sensor signal indicative of the user having modified the parameter to a desired extent, and (c) responsive to identifying the aspect of the first sensor signal, generate a new output signal, to direct the user to further modify the parameter of the voluntary action.

Alternatively or additionally, the circuitry is adapted to generate the output signal to direct the user to modify the parameter of the voluntary action, so as to facilitate an improvement in congestive heart failure of the user.

Alternatively or additionally, the circuitry is adapted to generate the output signal to direct the user to modify the parameter of the voluntary action, so as to facilitate treatment of a blood pressure disorder of the user.

Alternatively or additionally, the circuitry is adapted to generate the output signal to direct the user to modify the parameter of the voluntary action, so as to facilitate an improvement in asthma of the user.

Alternatively or additionally, the circuitry is adapted to generate the output signal to direct the user to modify the parameter of the voluntary action, so as to facilitate an improvement in cystic fibrosis of the user.

Alternatively or additionally, the circuitry is adapted to generate the output signal to direct the user to modify the parameter of the voluntary action, so as to facilitate an increase in mechanical compliance of arteries of the user.

Alternatively or additionally, the circuitry is adapted to generate the output signal to direct the user to modify the parameter of the voluntary action, so as to facilitate an increase in oxygenation of tissue of the user.

Alternatively or additionally, the circuitry is adapted to generate the output signal to direct the user to modify the parameter of the voluntary action, so as to facilitate weaning the user from a mechanical ventilator, reducing a duration of a post-surgery recover period of the user, reducing excessive sympathetic activity of the user, a modification of peristaltic activity of the user, a modification of vasomotor activity of the user, an increase of heart rate variability of the user, an increase of venous return to a heart of the user, a reduction of vasomotor tone of the user, a reduction of airway resistance of the user, an increase of endurance of an expiratory muscle of the user, an increase of blood flow in capillaries of the user, and/or a reduction of pain experienced by the user.

Alternatively or additionally, the apparatus includes a speaker, wherein the circuitry is adapted to drive the speaker to generate music, so as to direct the user to modify the parameter of the voluntary action.

Alternatively or additionally, the apparatus includes a speaker, wherein the circuitry is adapted to drive the speaker to output natural sounds, so as to direct the user to modify the parameter of the voluntary action.

Alternatively or additionally, the apparatus includes a screen, wherein the circuitry is adapted to drive the screen to display one or more patterns corresponding to the output signal, so as to direct the user to modify the parameter of the voluntary action.

Alternatively or additionally, the second sensor includes a blood pressure sensor, a photoplethysmographic sensor, a blood oximeter, an electrocardiographic sensor, and/or an electroencephalographic sensor.

Alternatively or additionally, the second sensor is adapted to measure heart rate of the user.

Alternatively or additionally, the second sensor includes an ultrasonic sensor, adapted to measure a cardiovascular variable.

Alternatively or additionally, the second sensor is adapted to measure a pulsatile change of volume of blood in an artery of the user, a non-pulsatile change of volume of blood in an artery of the user, a pulsatile change of volume of blood in tissue of the user, and/or a non-pulsatile change of volume of blood in tissue of the user.

Alternatively or additionally, the second sensor is adapted to non-invasively measure blood viscosity of the user.

Alternatively or additionally, the second sensor is adapted to measure the second physiological variable so as to facilitate a determination of a characteristic of peristalsis of the user.

Alternatively or additionally, the second sensor is adapted to measure the second physiological variable so as to facilitate a determination of arterial compliance of the user, pulse wave velocity of blood in blood vessels of the user, and/or a vasomotor frequency of the user.

Alternatively or additionally, the circuitry is adapted to set a frequency of the output signal responsive to the vasomotor frequency.

Alternatively or additionally, the first sensor includes a motion sensor.

Alternatively or additionally, the first sensor is adapted to be coupled to a limb of the user and to generate the first sensor signal responsive to motion of the limb.

Alternatively or additionally, the first sensor is adapted to measure a cyclic physiological variable of the user and to generate the first sensor signal responsive thereto, and wherein the circuitry is adapted to generate the output signal responsive to a desired change in a frequency of the cyclic physiological variable.

Alternatively or additionally, the first sensor includes a respiration sensor.

Alternatively or additionally, the apparatus includes a belt adapted to be placed around a torso of the user, wherein the respiration sensor is adapted to generate the first sensor signal responsive to a change in circumference of the torso.

Alternatively or additionally, the respiration sensor is adapted to measure a characteristic of the user's respiration so as to facilitate a determination of airway resistance of the user.

Alternatively or additionally, the respiration sensor is adapted to measure a characteristic of the user's respiration so as to facilitate a determination of a mechanical load against which the user breathes.

Alternatively or additionally, the circuitry is adapted to: (a) determine, responsive to the first signal, a current value of an Expiratory:Inspiratory (E:I) ratio of the user, (b) determine a desired final value of the E:I ratio, and (c) generate the output signal so as to direct the user to vary the user's E:I ratio from the current value thereof, through one or more intermediate values thereof, to the desired final value.

Alternatively or additionally, the circuitry is adapted to: (a) determine, responsive to the first signal, a current respiration rate of the user, (b) determine a desired final respiration rate, and (c) generate the output signal so as to direct the user to vary the user's respiration rate from the current value thereof, through one or more intermediate values thereof, to the desired final value.

Alternatively or additionally, the circuitry is adapted to: (a) determine, responsive to the first signal, a current value of an Expiratory:Inspiratory (E:I) ratio of the user, (b) determine a desired final value of the E:I ratio, and (c) generate the output signal so as to direct the user to vary the user's E:I ratio from the current value thereof, through one or more intermediate values thereof, to the desired final value, at generally the same time as directing the user to vary the respiration rate.

There is also provided, in accordance with a preferred embodiment of the present invention, apparatus for facilitating improving health of a user, including a stimulator, which is adapted to stimulate a portion of a body of the user at a stimulation rate between about 0.05 Hz and 0.15 Hz.

Preferably, the stimulator includes a pressure applicator, adapted to apply mechanical pressure, which varies at the stimulation rate, to the portion of the body.

Alternatively or additionally, the stimulator includes an electrode, adapted to apply electrical energy, which varies at the stimulation rate, to the portion of the body.

Alternatively or additionally, the stimulator includes a magnetic field generator, adapted to apply a magnetic field, which varies at the stimulation rate, to the portion of the body.

Alternatively or additionally, the stimulator includes a temperature-modifying unit, adapted to apply at the stimulation rate to the portion of the body at least one of: heating and cooling.

Alternatively or additionally, the stimulator includes an electromagnetic radiation emitter, adapted to apply electromagnetic radiation, which varies at the stimulation rate, to the portion of the body.

There is also provided, in accordance with a preferred embodiment of the present invention, apparatus for facilitating improving health of a user, including:

a sensor, adapted to measure a physiological variable of the user and to generate a sensor signal responsive thereto;

a processor, adapted to receive the sensor signal and to determine, responsive thereto, a frequency of variation of a cardiovascular variable of the user that lies between about 0.05 Hz and 0.15 Hz; and a stimulator, adapted to stimulate the user at the determined frequency.

Preferably, the sensor includes a first sensor, wherein the apparatus includes a second sensor, adapted to measure a second physiological variable and to convey to the processor a second sensor signal responsive thereto, and wherein the processor is adapted to drive the stimulator to stimulate the user so as to obtain a desired value of the second sensor signal.

Alternatively or additionally, the stimulator includes a pressure applicator, adapted to apply to the user mechanical pressure, which varies at the determined frequency.

There is also provided, in accordance with a preferred embodiment of the present invention, apparatus for facilitating improving health of a user, including:

a sensor, adapted to measure a physiological variable of the user and to generate a sensor signal responsive thereto; and circuitry, adapted to receive the sensor signal and to generate responsive thereto, for presentation to the user, two or more acoustic signals which are configured so as to create a spatial sound effect.

Preferably, the circuitry is adapted to configure the acoustic signals so as to create a stereo sound effect.

Alternatively or additionally, the circuitry is adapted to configure the acoustic signals so as to create a three-dimensional sound effect.

Alternatively or additionally, the sensor includes a first sensor, adapted to measure a first physiological variable, which is indicative of a voluntary action of the user, wherein the apparatus includes a second sensor, adapted to measure a second physiological variable, which is not entirely under the direct voluntary control of the user, and wherein the circuitry is adapted to respective first and second sensor signals from the first and second sensors and, responsive thereto, to generate the acoustic signals, so as to direct the user to modify a parameter of the voluntary action.

Alternatively or additionally, the circuitry is adapted to generate the acoustic signals such that an aspect of the spatial effect, selected from the list consisting of: a vertical aspect and a horizontal aspect, corresponds to the parameter of the voluntary action.

Alternatively or additionally, the circuitry is adapted to generate the acoustic signals such that (a) a first sound generated responsive thereto is perceived by the user as coming from a first location and corresponds to a direction to the user to exhale, and (b) a second sound generated responsive to the acoustic signals is perceived by the user as coming from a second location which is higher than the first location, the second sound corresponding to a direction to the user to inhale.

Alternatively or additionally, the circuitry is adapted to generate the acoustic signals such that sounds generated responsive thereto, which are perceived by the user as coming from left and right sides of the user, correspond to respective directions to the user to move respective left and right legs of the user.

There is also provided, in accordance with a preferred embodiment of the present invention, apparatus for measuring blood pressure of a user, including:

a blood pressure sensor, adapted to take first and second blood pressure measurements and to generate respective first and second blood pressure signals responsive to the measurements, a time period between the first and second measurements being less than about 30 minutes; and a processor, adapted to receive the first and second blood pressure signals, to determine a discrepancy therebetween, and to automatically actuate the blood pressure sensor to take a third blood pressure measurement if the discrepancy is greater than a determined threshold.

There is also provided, in accordance with a preferred embodiment of the present invention, apparatus for measuring blood pressure of a user, including:

a blood pressure sensor, adapted to make n measurements of systolic blood pressure (S) and diastolic blood pressure (D) of the user, thereby defining a measurement set M having n elements $\{(S_1, D_1), (S_2, D_2), \ldots, (S_n, D_n)\}$; and a processor, adapted to process measurement set M, so as to determine a statistical relation among the elements of measurement set M, and adapted to assess, responsive to the relation, a test measurement of systolic and diastolic blood pressure, so as to determine whether to identify a test element $(S_{test}, D_{test})$, corresponding to the test measurement, as an outlier with respect to the elements of measurement set M.

Preferably, the processor is adapted to determine a regression among the elements of measurement set M, such as a linear regression.

There is also provided, in accordance with a preferred embodiment of the present invention, apparatus for measuring and modifying blood pressure of an ambulatory user outside of a healthcare facility, including:

a blood pressure sensor, adapted to make a plurality of measurements of the blood pressure of the ambulatory user during a time period spanning at least about a week, and to generate respective blood pressure signals responsive to each of the measurements;

an intervention unit, adapted to administer an intervention to the ambulatory user a plurality of times during the time period, so as to modify the user's blood pressure; and a processor, adapted to receive the blood pressure signals from the sensor, analyze the signals, and automatically modify a parameter of the intervention responsive to analyzing the signals.

Preferably, the processor is adapted to (a) perform a statistical analysis on the signals, (b) identify one or more of the measurements as outliers with respect to the other measurements, and (c) automatically modify the parameter of the intervention responsive to measurements not identified as outliers.

Alternatively or additionally, the processor is adapted to (a) calculate a regression based on a measurement set of systolic and diastolic blood pressure measurements $(S_i, D_i)$, (b) identify as outliers one or more of the measurements in the measurement set responsive to calculating the regression, and (c) automatically modify the parameter of the intervention responsive to measurements not identified as outliers.

There is also provided, in accordance with a preferred embodiment of the present invention, apparatus for measuring and modifying a physiological variable of an ambulatory user outside of a healthcare facility, including:

a photoplethysmographic (PPG) sensor, adapted to make a plurality of measurements of the ambulatory user during a time period spanning at least about a week, and to generate respective PPG signals responsive to each of the measurements;

an intervention unit, adapted to administer an intervention to the ambulatory user a plurality of times during the time period, so as to improve a future PPG measurement; and a processor, adapted to receive the PPG signals from the sensor, analyze the signals, and automatically modify a parameter of the intervention responsive to analyzing the signals.

There is also provided, in accordance with a preferred embodiment of the present invention, apparatus for measuring mechanical deformation, including:

a housing;

a base electrode; and a deformable electrode, mechanically coupled to the base electrode and to the housing, the base electrode and the deformable electrode defining a capacitor having capacitance, such that the capacitance is varied responsive to deformation of the deformable electrode.

Preferably, a portion of the base electrode is adapted to be at a substantially fixed distance from a portion of the deformable electrode.

Alternatively or additionally, the deformable electrode is adapted to be coupled to a user, so as to deform responsive to respiration of user.

Alternatively or additionally, the apparatus includes a member, mechanically coupled to the deformable electrode, such that movement of the member deforms the deformable electrode and varies the capacitance.

Alternatively or additionally, the apparatus includes a belt, adapted to be placed around a torso of a user and to cause movement of the member responsive to a change in circumference of the torso.

Alternatively or additionally, the member is adapted to be in physical contact with the deformable electrode.

There is also provided, in accordance with a preferred embodiment of the present invention, apparatus for facilitating improving health of a user, including:

a first sensor, adapted to measure a first physiological variable, which is indicative of an action of the user;

a second sensor, adapted to measure a second physiological variable, which is not entirely under the direct voluntary control of the user; and circuitry, adapted to receive respective first and second sensor signals from the first and second sensors, and, responsive thereto, to generate an output signal which causes the user to modify, substantially unintentionally, a parameter of the action.

Preferably, the first sensor includes a respiration sensor, a blood pressure sensor, and/or a photoplethysmographic sensor.

Alternatively or additionally, the circuitry is adapted to generate a musical signal which causes the user to modify, substantially unintentionally, the parameter of the action.

Alternatively or additionally, the circuitry is adapted to generate the output signal while the user sleeps.

There is also provided, in accordance with a preferred embodiment of the present invention, apparatus for generating music, including:

a sensor, adapted to receive a rhythm signal corresponding to a rhythm of a cyclic physiological activity of a user, the physiological activity having first and second activity phases thereof;

a processor, adapted to analyze the rhythm signal to determine a frequency thereof and to determine a new frequency responsive to a desired change of the frequency of the rhythm signal; and circuitry, adapted to:

generate at the new frequency a music signal for presentation to the user, the music signal having first and second music phases thereof respectively corresponding to the first and second activity phases, a duration of each of the music phases expressible as being approximately equal to an integer multiple of a base duration, the integer multiple being less than or equal to four, so as to direct the user to modify durations of the first and second activity phases responsive to the respective durations of the first and second music phases.

There is also provided, in accordance with a preferred embodiment of the present invention, apparatus for generating music, including:

a sensor, adapted to receive a rhythm signal corresponding to a rhythm of a cyclic physiological activity of a user, the physiological activity having first and second activity phases thereof;

a processor, adapted to analyze the rhythm signal to determine a frequency thereof and to determine a new frequency responsive to a desired change of the frequency of the rhythm signal; and circuitry, adapted to:

generate at the new frequency a music signal for presentation to the user, the music signal having first and second music phases thereof respectively corresponding to the first and second activity phases, a duration of one of the music phases being approximately equal to an integer multiple of a duration of the other one of the music phases, so as to direct the user to modify durations of the first and second activity phases responsive to the respective durations of the first and second music phases.

There is also provided, in accordance with a preferred embodiment of the present invention, apparatus for generating music, including:

a sensor, adapted to receive a rhythmic physiological pattern corresponding to a rhythm of a physiological activity of a user;

a processor, adapted to analyze the rhythmic physiological pattern to determine an actual activity pattern thereof and to determine a new activity pattern responsive to a desired change of the actual activity pattern; and circuitry, adapted to:

generate a music signal for presentation to the user, the music signal having two or more sets of notes, at least one of the sets of notes having a rhythmic characteristic corresponding to the new activity pattern, so as to direct the user to modify the rhythm of the physiological activity responsive to the music signal.

There is also provided, in accordance with a preferred embodiment of the present invention, apparatus for generating music, including:

a sensor, adapted to receive a rhythm signal corresponding to a rhythm of a cyclic physiological activity of a user;

a processor, adapted to analyze the rhythm signal to determine a pattern thereof and to determine a new pattern responsive to a desired change of the pattern of the rhythm signal; and circuitry, adapted to:

generate, responsive to the new pattern, a music signal for presentation to the user; and determine, responsive to a characteristic of the new pattern, a set of music layers to include in the music signal, the layers having notes, such that the notes of one of the layers are played at a generally faster rate than the notes of another one of the layers, so as to direct the user to modify the rhythm of the physiological activity responsive to the music signal.

There is also provided, in accordance with a preferred embodiment of the present invention, a method for facilitating improving health of a user, including:

receiving a first physiological variable, which is indicative of a voluntary action of the user;

receiving a second physiological variable, which is not entirely under the direct voluntary control of the user;

generating an output signal, responsive to the first and second variables; and directing the user to modify a parameter of the voluntary action responsive to the output signal.

There is also provided, in accordance with a preferred embodiment of the present invention, a method for facilitating improving health of a user, including stimulating a portion of a body of the user at a stimulation rate between about 0.05 Hz and 0.15 Hz.

There is also provided, in accordance with a preferred embodiment of the present invention, a method for facilitating improving health of a user, including:

measuring a physiological variable of the user; and determining, responsive to measuring, a frequency of variation of a cardiovascular variable of the user that lies between about 0.05 Hz and 0.15 Hz; and stimulating the user at the determined frequency.

There is also provided, in accordance with a preferred embodiment of the present invention, a method for facilitating improving health of a user, including:

measuring a physiological variable of the user; and generating, responsive thereto, for presentation to the user, two or more acoustic signals which are configured so as to create a spatial sound effect.

There is also provided, in accordance with a preferred embodiment of the present invention, a method for measuring blood pressure of a user, including:

making first and second blood pressure measurements, a time period between the first and second measurements being less than about 30 minutes;

determining a discrepancy between the first and second measurements; and automatically making a third blood pressure measurement if the discrepancy is greater than a determined threshold.

There is also provided, in accordance with a preferred embodiment of the present invention, a method for measuring blood pressure of a user, including:

making n measurements of systolic blood pressure (S) and diastolic blood pressure (D) of the user, thereby defining a measurement set M having n elements $\{(S_1, D_1), (S_2, D_2), \ldots, (S_n, D_n)\}$; and processing measurement set M, so as to determine a statistical relation among the elements of measurement set M;

assessing, responsive to the relation, a test measurement of systolic and diastolic blood pressure; and determining, responsive to assessing, whether to identify a test element $(S_{test}, D_{test})$, corresponding to the test measurement, as an outlier with respect to the elements of measurement set M.

There is also provided, in accordance with a preferred embodiment of the present invention, a method for measuring and modifying blood pressure of an ambulatory user outside of a healthcare facility, including:

making a plurality of measurements of the blood pressure of the ambulatory user during a time period spanning at least about a week;

administering an intervention to the ambulatory user a plurality of times during the time period, so as to modify the user's blood pressure; and analyzing the measurements; and automatically modifying a parameter of the intervention responsive to analyzing the signals.

There is also provided, in accordance with a preferred embodiment of the present invention, a method for measuring mechanical deformation, including mechanically coupling a base electrode to a deformable electrode, the base electrode and the deformable electrode defining a capacitor having capacitance, such that the capacitance is varied responsive to deformation of the deformable electrode.

There is also provided, in accordance with a preferred embodiment of the present invention, a method for facilitating improving health of a user, including:

measuring a first physiological variable, which is indicative of an action of the user;

measuring a second physiological variable, which is not entirely under the direct voluntary control of the user; and generating an output signal which causes the user to modify, substantially unintentionally, a parameter of the action.

The present invention will be more fully understood from the following detailed description of the preferred embodiments thereof, taken together with the drawings, in which:

DETAILED DESCRIPTION OF PREFERRED EMBODIMENTS

Figure 1:
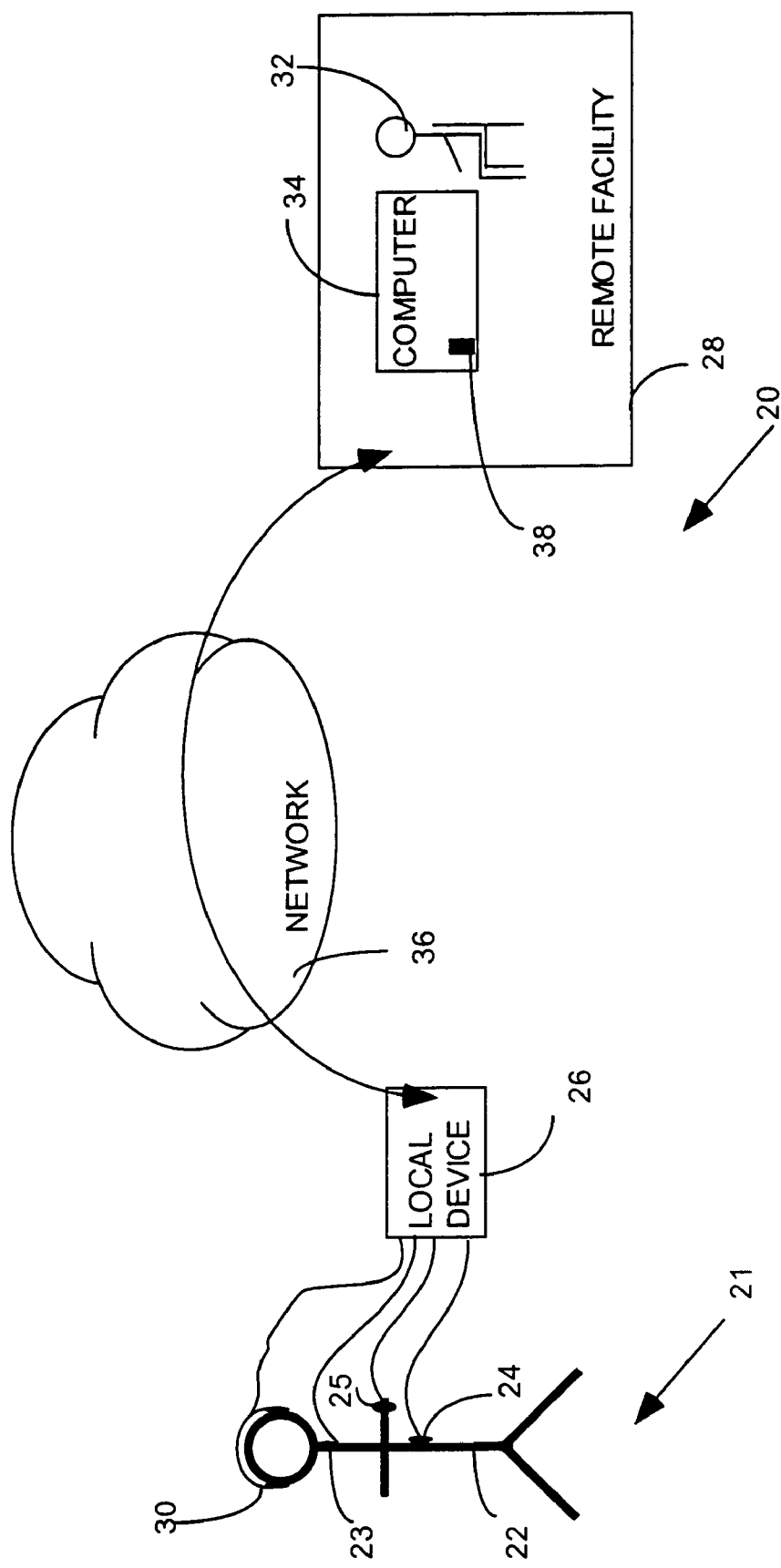
FIG. 1 is a schematic illustration of an interventive-diagnostic system, according to a preferred embodiment of the present invention.

FIG. 1 is a schematic illustration of an interventive-diagnostic system 20, according to a preferred embodiment of the present invention. System 20 comprises a local computing device 26, which receives signal data from sensors 23, 24 and 25 coupled to a user 22 at a local site 21. Typically, at least some of the signal data represents biorhythmic activity of user 22. The signal data comprise signals from one or more health status sensors 23, one or more biorhythmic-activity sensors 24 and/or one or more benefit-related sensors 25. Local device 26, the sensors, and the signal data received by the local device are described in greater detail hereinbelow. The connection between local device 26 and sensors 24 and 25 may be wired or wireless.

Local device 26 performs a first analysis on the received signals to generate a set of analyzed data, which is transferred to a remote facility 28, such as a hospital or medical clinic. A program operator 32 and a computer 34, controlled by operator 32, are preferably located at the facility. Remote facility 28 is physically distant from local device 26 and user 22. Preferably, remote facility 28 communicates with local device 26 via a distributed network 36 such as the Internet. Alternatively or additionally, program operator 32 and/or computer 34 communicate with local device 26 and/or user 22 by other means known in the art, for example by a telephone modem or by voice, using a telephone.

Operator 32 and/or computer 34 preferably further analyze the data set received from local device 26, generating a result which is transmitted to local site 21 and preferably saved in a memory 38 of computer 34. For example, the result from remote facility 28 may be verbal help to enable user 22 to modify operation of device 26, or the remote result may be data communication to the local device. Local device 26 utilizes the result from the remote facility, and/or the set of analyzed data, and/or the signals received from sensors 24 and 25, to generate an intervention which is provided to user 22 via a stimulation unit 30. The intervention typically comprises an intelligible sensory input stimulus, such as a sound pattern provided through earphones worn by user 22, a dynamic graphic pattern provided on a screen visible to the user, or a regularly repeating audio and/or visual pattern, such as a metronome. The stimulus preferably changes at least one aspect of the biorhythmic activity of user 22.

Figure 2:
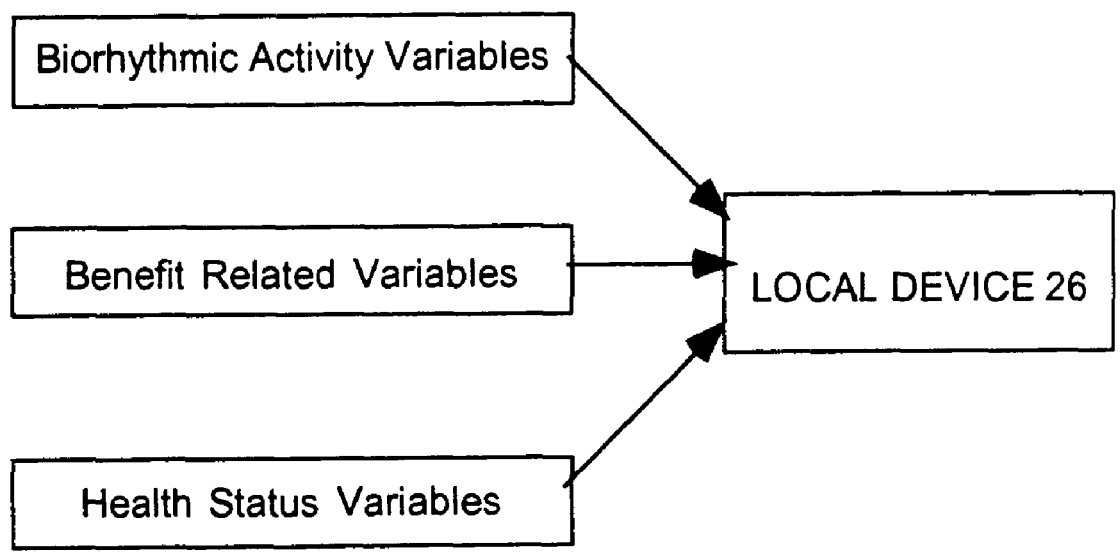
FIG. 2 is a schematic block diagram of inputs to a local computing device of the interventive-diagnostic system of FIG. 1, according to a preferred embodiment of the present invention.

FIG. 2 is a schematic block diagram of categories of variables which are typically input as signals or data to local device 26, according to a preferred embodiment of the present invention. A first category, herein termed biorhythmic-activity variables, comprises signals generated by a biorhythmic activity of user 22, wherein the biorhythmic activity is one which may be modified by the user. For example, biorhythmic activity variables may be signals generated by an appropriate sensor in response to the breathing of user 22, or in response to eye-blinking, or in response to flexure and/or rigidity of one or more voluntary or semi-voluntary muscles of the user. Biorhythmic-activity signals are measured by one or more appropriate biorhythmic-activity sensors, such as a force transducer for monitoring breathing movements via changes in chest or abdominal circumference, based on a strain-gauge which is attached to an elastic belt, such as that described by Gavish in the above-cited U.S. Pat. No. 5,423,328. Preferably, the one or more biorhythmic-activity sensors are self-installed by user 22.

A second category of variables, herein termed benefit-related variables, comprises signals generated by measurements of physiological variables of user 22, wherein the variables cannot normally be modified by the user at will. Typically, benefit-related variables include parameters of the user that are altered by a pathology or other phenomenon of user 22 which is being treated by device 26. For example, benefit-related variables may be those corresponding to blood pressure, blood oxygenation (e.g., SpO2), pulse-wave velocity, variations in skin blood volume (e.g., as measured by photoplethysmography), respiration parameters (e.g., peak air flow), or an electrocardiogram (ECG) measurement of user 22. Benefit-related variables are measured by one or more appropriate benefit-related sensors, such as a sphygmomanometer, a pulse oximeter, or an electrocardiograph, which are preferably self-installed by user 22. Alternatively, the one or more benefit-related sensors are installed by someone other than user 22, such as a parent, if user 22 is a child. Additionally, benefit-related variables may be monitored continuously or at specific time points, such as when measuring blood pressure by a standard sphygmomanometer.

A third category of variables, herein termed health status variables, comprise data which give details of the general state of user 22. For example, health status variables typically comprise weight, height, age, resting respiration rate, and resting heart rate of user 22, as well as the user's ECG and blood pressure, measured during an intervention session. As appropriate, device 26 evaluates the health status variables to determine whether they are within safe ranges. For example, for a user having a specified gender, age, and weight, a certain measured heart rate may be determined to be too high or too low, and thus force a premature termination of the intervention and an alarm signal.

Preferably, some of the health status variables are input to local device 26 via a keyboard which may be coupled to or integrated with device 26. Alternatively or additionally, health status variables may be input to device 26 by connecting the device to a computer. Furthermore health status variables may be input to device 26 by an appropriate sensor, such as an electronic weigh-scale, when the variable to be input is weight. Storage and evaluation of changes of the health status variables can be used to determine a trend in the user's medical condition, as described hereinbelow.

Figure 3:
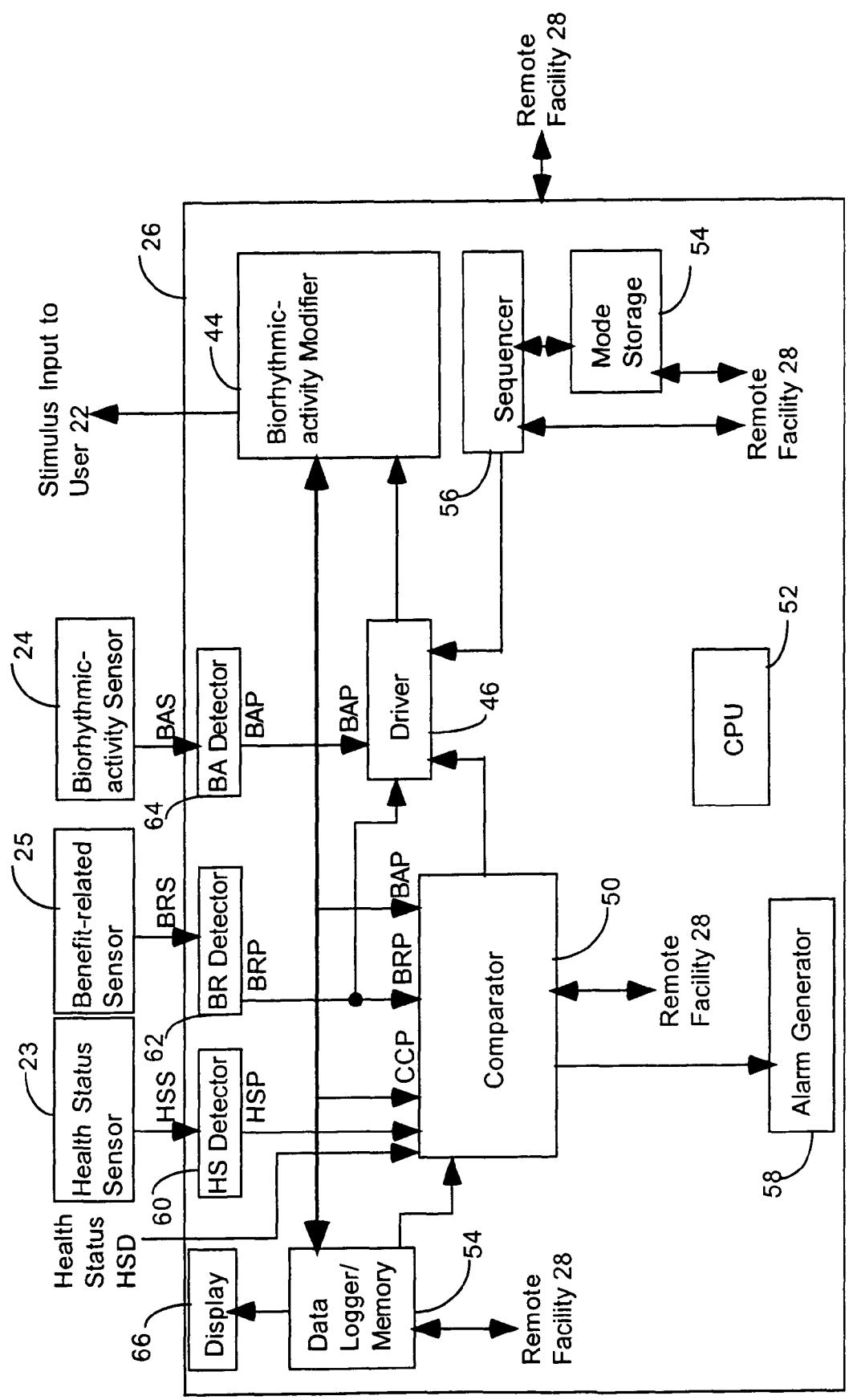
FIG. 3 is a schematic block diagram showing the local computing device of the interventive-diagnostic system of FIG. 1, according to a preferred embodiment of the present invention.

FIG. 3 is a schematic block diagram showing components of local device 26, according to a preferred embodiment of the present invention. Generally, local device 26 generates intervention parameters responsive to input signals, and provides a stimulus via stimulation unit 30 to user 22, responsive to the intervention parameters. Local device 26 is preferably implemented in discrete components or a combination of discrete and custom or semi-custom components. Alternatively, device 26 is implemented by operating a program on an industry-standard computer coupled to a display monitor.

Device 26 comprises a central processing unit (CPU) 52, which is coupled to and controls the operation of the individual components of device 26 described hereinbelow. For clarity, lines are not shown between CPU 52 and the other components. It will be appreciated that there are many ways within the scope of the present invention to achieve objects of the invention, and the particular components and methods described with respect to FIG. 2 are an example of these. A biorhythmic activity detector 64 receives a biorhythmic-activity signal, herein designated BAS, from sensor 24, and generates an output responsive to BAS, representing one or more pattern components of the sensed biorhythmic activity of the user. Pattern components and other relevant concepts for implementing detector 64 are described in the above-cited U.S. Pat. No. 5,076,281 and U.S. Pat. No. 5,800,337. Preferably, the output of detector 64 includes intervention parameters, herein termed biorhythm activity parameters (BAP), which are of a quantitative nature. A benefit related detector 62 receives a benefit-related signal, herein designated BRS, from sensor 25, and generates an output responsive to BRS representing one or more pattern components of the sensed benefit-related signals of the user. Preferably, the output of detector 62 includes intervention parameters, herein termed benefit-related parameters (BRP), which are of a quantitative nature.

A health status detector 60 receives health status data, herein designated HSD, by methods described above, and generates an output responsive to the HSD representing one or more components of the health status of the user. Preferably, the output of detector 60 includes current values relating to one or more physiological variables that may be altered by application of embodiments of the present invention. These values are herein termed health status parameters (HSP), and are typically of a quantitative nature. Intervention parameters BAP, BRP, and HSP most preferably comprise specific time-point analyses of their respective signals, which are used to identify special points characterizing the signals' structures, such as maxima, minima, and turning points (e.g., as described by Gavish in U.S. Pat. No. 5,800,337). A further set of parameters, herein termed cross-correlation parameters (CCP), are derived by correlating BAS, BRS, and HSP signals, so as generate a cross-correlation and a cross-spectral analysis of the signals. Most preferably, values of BAS, BAP, BRS, BRP, HSS, HSP, and CCP are stored in a data logger/memory 54, which preferably comprises industry-standard volatile and non-volatile memory components.

A comparator 50 receives values of BAP, BRP, HSP, and CCP in order to compare the values against values which have been previously stored in data logger 54. The operation of comparator 50 is described in detail hereinbelow, with reference to FIG. 4. If the values of BAP, BRP, HSP, and CCP are within predefined limits, comparator 50 enables a driver 46, whose function is to operate a biorhythmic activity modifier 44. Preferably, driver 46 operates by providing a set of operational command inputs to modifier 44 so as to cause a component of the stimulus input to the user to be related to a component of the existing biorhythmic activity of user 22 which is sensed by one or more of sensors 23, 24, and/or 25. Comparator 50 is also able to activate an alarm generator 58, in the event that one or more of the health status parameters and/or benefit-related parameters are outside a predefined range.

A mode storage component 54 stores a plurality of modes under which device 26 is able to operate, which modes are described in greater detail below with respect to FIG. 6. A sequencer 56 interacts with mode storage 54 so as to choose a sequence of modes which is to be utilized by driver 46 in operating biorhythmic activity modifier 44. Both mode storage 54 and sequencer 56 are addressable by remote facility 28, most preferably by interfacing with CPU 52 (as described above for device 26, with reference to FIG. 1), so that sequences of operational modes may be updated. Operational mode sequences may be modified for a number of reasons, for example, to optimize a particular therapeutic strategy, to abandon a strategy that is not producing desired results, or simply to keep user 22 interested. A display 66, most preferably an industry-standard alphanumeric display, displays to user 22 data corresponding to signals and parameters described hereinabove, as well as other data such as help signals, according to commands received from CPU 52.

Biorhythmic activity modifier 44 receives parameters BAP and BRP, respectively from detectors 62 and 64 and/or from driver 46, and provides user 22 with a stimulus input which is able to change at least one aspect of the user's biorhythmic activity. For example, the stimulus input provided to user 22 may be a sound pattern, which varies over time to teach user 22 to alter a time period associated with inhaling and/or exhaling.

In some applications, program operator 32 and/or computer 34 interact with components of local device 26, other than as described above, so as to be able to follow and vary the operation of device 26. Program operator 32 and/or computer 34 are able to read data from, and write data to, data logger/memory 54, and also to overwrite any of the data stored in data logger/memory 54. Preferably, threshold values determined at remote facility 28 are supplied to comparator 50, which are used by the comparator to perform comparisons described hereinbelow, and which are herein termed criteria via threshold (CRT) values.

Figure 4:
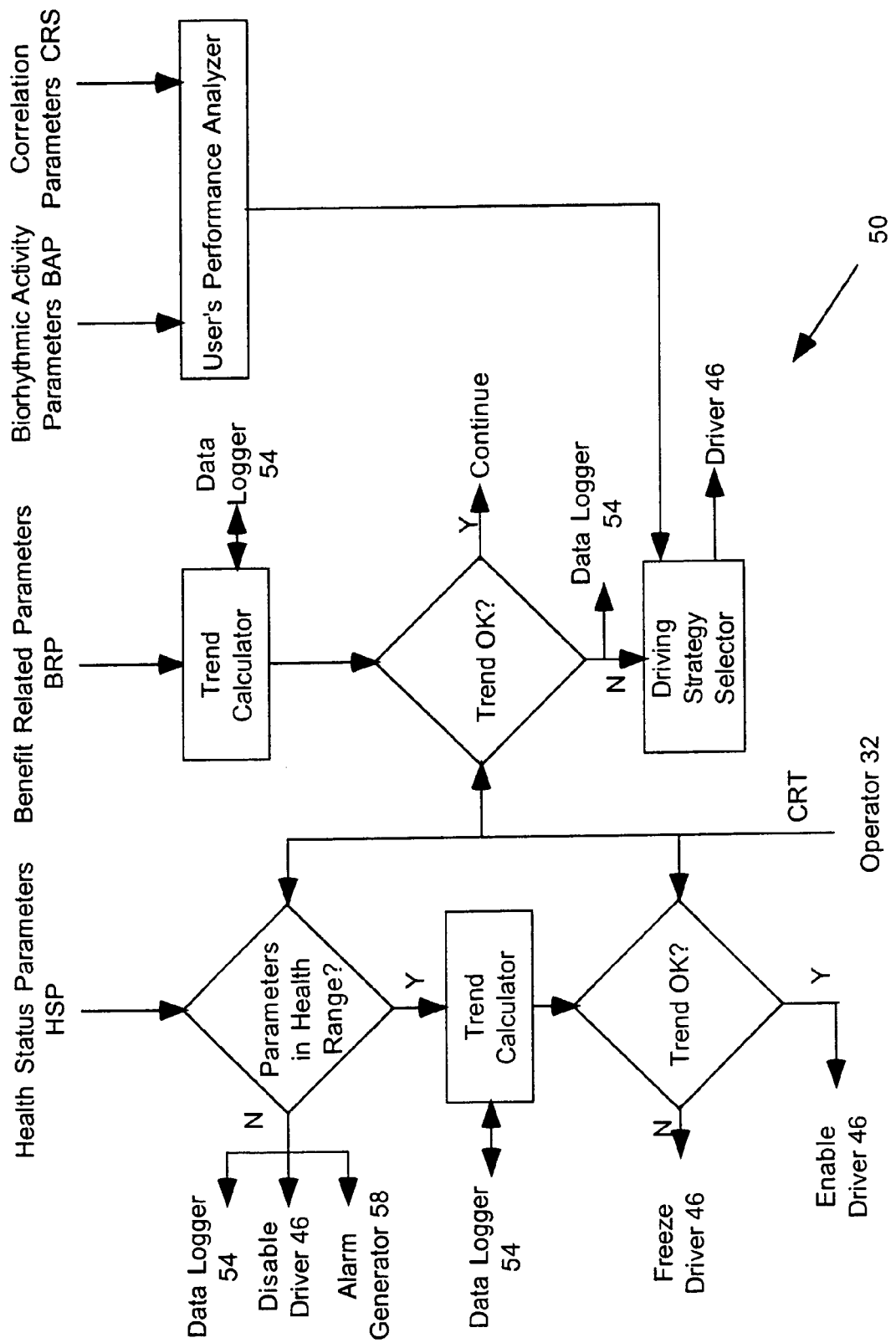
FIG. 4 is a flow chart of a comparator of the local computing device, according to a preferred embodiment of the present invention.

FIG. 4 is a flow chart showing operation of comparator 50, according to a preferred embodiment of the present invention. Typically, health status parameters HSP are compared with CRT values which are input to a health range decider. If the values are outside the health range delineated by the CRT values, alarm generator 58 is triggered, driver 46 is disabled, and a signal announcing the out-of-range state is sent to data logger 54. If parameters HSP are within range, they are used, together with previous HSP parameters from data logger 54, in order to calculate an updated HSP trend. The new trend is checked to see if it is within acceptable limits, using HSP trend criteria derived from the CRT values. If the HSP trend is in within acceptable limits, driver 46 is enabled. If the HSP trend is not within acceptable limits, driver 46 is disabled. The trend of a parameter may be evaluated by analyzing repeated measurements thereof over a prescribed period. Preferably, the analysis comprises a statistical analysis, such as calculating a regression to determine a slope and to know the statistical significance of the determined slope. Alternatively or additionally, other curve-fitting methods known in the art may be used.

Benefit-related parameters BRP are used, together with previous BRP parameters from data logger 54, in order to calculate an updated BRP trend. The new trend is checked to see if it is within an acceptable range, using BRP trend criteria derived from the CRT values. If the BRP trend is within the acceptable range, no further action is taken by device 26. Otherwise, a signal announcing the out-of-range state is sent to data logger 54, and a driving strategy selector is informed. The driving strategy selector determines which parameters of driver 46 are to be modified, to what degree, and in what manner. In order to make its determination, the selector also receives an analysis of the performance of user 22. The analysis is performed by comparing the BAP parameters with the CCP parameters generated by detector 62, and may be responsive to inputs from remote facility 28.

Figure 5:
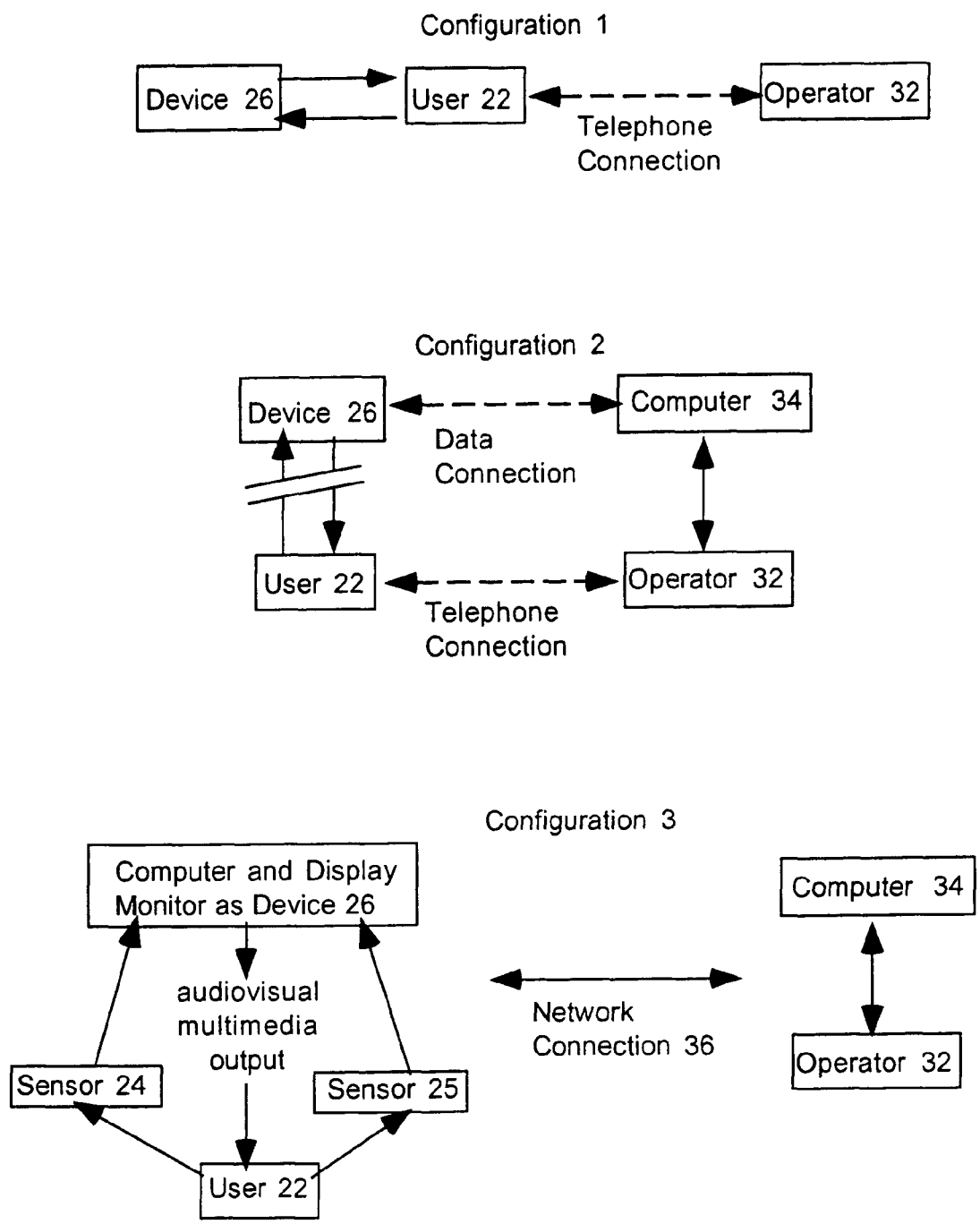
FIG. 5 is a schematic diagram illustrating a number of possible configurations of the interventive-diagnostic system of FIG. 1, according to a preferred embodiment of the present invention.

FIG. 5 is a schematic diagram illustrating a number of possible configurations of system 20, according to a preferred embodiment of the present invention. In a first configuration, user 22 is coupled to device 26 as described hereinabove with reference to FIG. 1. While user 22 is operating device 26, the user contacts remote facility 28 and relays the data displayed by display 66 to program operator 32. Most preferably, user 22 contacts operator 32 by telephone, and verbally relates the data shown on the display. Program operator 32 analyzes the relayed data, and verbally informs user 22 of the results of the analysis, whereupon, depending on the results, user 22 may be instructed to make adjustments to device 22. It will be appreciated that a configuration such as that illustrated is especially useful when device 26 is operated by user 22 as a generally self-contained unit, wherein user 22 requires help and/or instruction in operating the device and modifying parameters thereof.

In a second configuration, user 22 sets device 26 to communicate directly with computer 34 in remote facility 28, during an intervention session, or following one or more sessions. User 22 contacts program operator 32, preferably via telephone, to inform the operator that device 26 is connected, whereupon the operator is able to download and inspect data from components of device 26, such as data in data logger 54. Alternatively or additionally, program operator 32 is able to alter settings of device 26, for example, by uploading new music or new values of CRT parameters to the device, and is also able to communicate verbally with user 22. This configuration is useful when device 26 is to be checked and/or updated by operator 32 on an intermittent basis. The configuration is also useful for enabling program operator 32 to inform user 22 of his progress, based on data stored in device 26.

In a third configuration, device 26 preferably comprises a local industry-standard personal computer coupled to a display monitor, as described hereinabove with respect to FIG. 3. One or more of sensors 23, 24 and/or 25 are coupled to the local computer. The local computer communicates with computer 32 at remote facility 28, preferably via network 36, so that, for example, a new audiovisual multimedia output is able to be transmitted from the remote facility to the local computer. In addition, program operator 32 is able to communicate with user 22, for example by telephone as described above, and/or by an industry-standard network communication program installed on the local computer and on computer 32, such as a chat program. This configuration is useful when full two-way continuous communication between remote facility 28, user 22, and device 26 is required. In this configuration, for example, messages, data reports, and verbal and non-verbal information may be exchanged.

Figure 6:
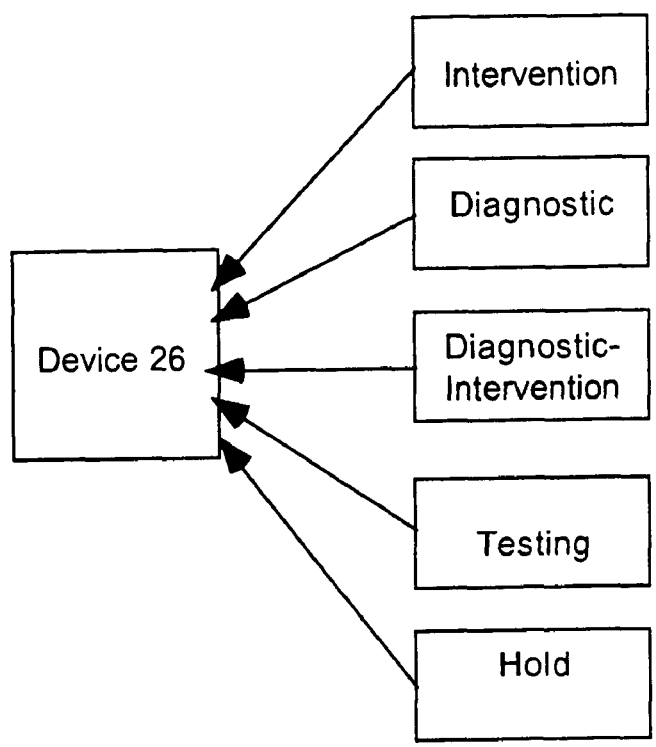
FIG. 6 is a schematic block diagram showing a number of possible modes in which the local computing device is able to operate, according to a preferred embodiment of the present invention.

FIG. 6 is a schematic block diagram showing a number of possible operational modes of local device 26, according to a preferred embodiment of the present invention. Most preferably, mode storage component 54 holds parameters corresponding to the modes described hereinbelow. In an intervention mode, device 26 generates a stimulus for user 22, with the intention of modifying a variable of user 22. In a diagnostic mode, device 26 performs one or more measurements of a variable of user 22, without modifying the variable. In a diagnostic-interventive mode, device 26 initiates an intervention and performs a diagnosis, or repeatedly cycles between diagnosis and intervention in any desired pattern. In a testing mode, device 26 executes a programmed sequence of interventions and/or diagnoses, in order to characterize physiological variables of user 22. Most preferably, sequencer 56 stores a plurality of programmed sequences. In a hold mode, device 26 is placed into a waiting state until activated by an action of user 22 or remote facility 28.

Examples of modes which typically are applicable to users with congestive heart failure, although the modes may also be applied to other users, are described in Table I hereinbelow. A notation which may be used to characterize the mode is also given in the table.

TABLE I

| Mode | Notation | Description |
| --- | --- | --- |
| Intervention 1 | I1 (RR) | Slow down breathing pattern using a musical pattern stimulus. The pattern is implemented interactively, at a breathing rate (RR breaths per minute) set by a predetermined algorithm. |
| Intervention 2 | I2 (RR, T) | Entrain breathing at a rate of RR breaths per minute, for a period of T minutes. |
| Diagnosis 1 | D1 (C) | Measure and record parameters based on breathing. When C = 1, record signals and parameters in data logger 54. When C = 0, record only parameters in the data logger. |
| Diagnosis 2 | D2 (C) | Measure and record parameters based on breathing and pulse oximetry. |
| Diagnostic-Interventive 1 | DI1 | Perform D1 (1) followed by I1, so as to measure long-term benefit parameters, and then perform a therapeutic intervention. |
| Testing 1 | T1 | A sequence [D2, I2 (15, 2), I2 (10, 2), I2 (16, 2), D2] measures acute response to intervention, to characterize parameters of the cardiovascular control system. |

Examples of modes which typically are applicable to users who are asthmatic children, although the modes may be applied to other users, are described in Table II hereinbelow.

TABLE II

| Mode | Notation | Description |
| --- | --- | --- |
| Intervention 3 | I3 | Present scenes including a psychological stressor, e.g., in the context of a video game. |
| Intervention 4 | I4 | Present "neutral" scenes, without a psychological stressor. |
| Diagnosis 3 | D3 | Measure and record breathing-related parameters. |
| Testing 2 | T2 (1) | Perform a sequence [D3, I1 (1), D3] to measure acute response to the intervention, and to characterize physiological variables which are sensitive to the stressor. |

Figure 7:
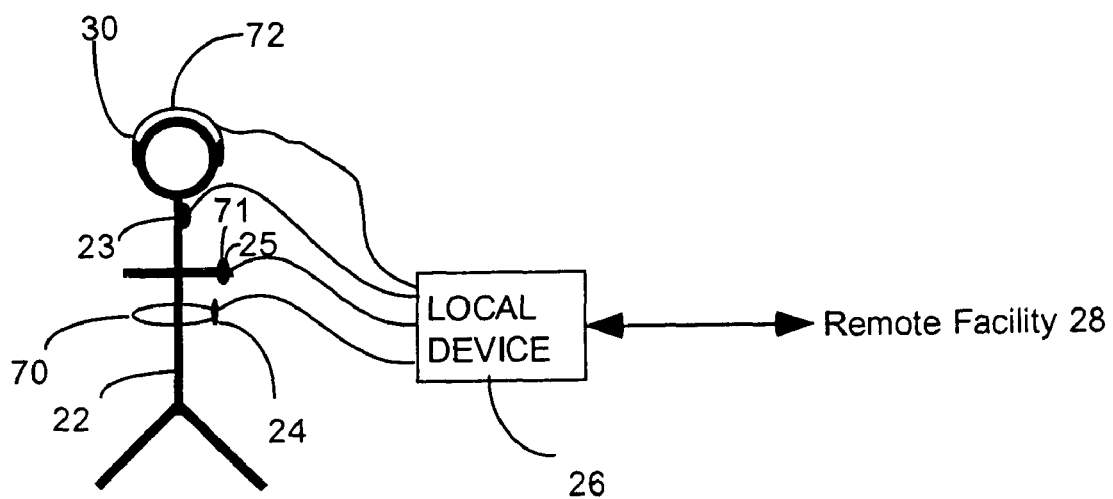
FIG. 7 is a schematic illustration showing how the interventive-diagnostic system of FIG. 1 is applied to a congestive heart failure patient, according to a preferred embodiment of the present invention.

FIG. 7 is a schematic illustration showing system 20 applied to a congestive heart failure patient, according to a preferred embodiment of the present invention. Sensor 24 preferably comprises a force transducer/respiration sensor 70 (such as the force transducer described hereinabove with reference to FIG. 2), coupled to a belt placed around the chest of user 22, who is a congestive heart failure patient. Sensor 25 comprises a pulse oximeter 72, which is placed on a finger of user 22. Such sensors, and their method of application and use, are well known in the art. Stimulation unit 30 preferably comprises a set of earphones 72 worn by user 22, which provide a music-like pattern according to outputs from biorhythmic activity modifier 44. Alternatively or additionally, unit 30 comprises an external speaker, for example, the loudspeaker of a personal computer. Device 26 uses input signals from sensor 70 to generate biorhythmic activity parameters corresponding to a respiration rate, an inspiration time, an expiration time, and a desired graded performance of user 22. Device 26 also makes measurements of benefit-related parameters derived from pattern classification statistics, such as a percentage of time spent in a pathological breathing state, oxygen saturation levels and their fluctuations, and heart rate.

Figure 8:
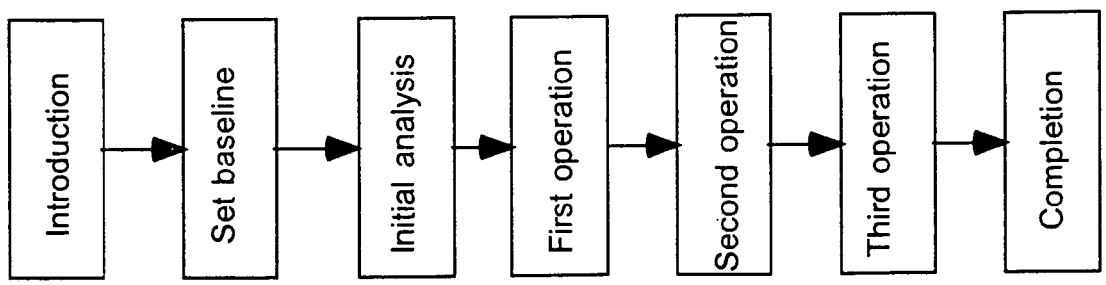
FIG. 8 is a schematic flow chart showing steps involved in a rehabilitation program for the patient described with reference to FIG. 7, according to a preferred embodiment of the present invention.

FIG. 8 is a schematic flow chart showing steps involved in a rehabilitation program for the patient described with reference to FIG. 7, according to a preferred embodiment of the present invention. Preferably, remote facility 28 and user 22 operate in configuration 1, as described hereinabove. In an introduction step, operator 32 introduces user 22 to device 26 and the program described hereinbelow. Operator 32 also determines appropriate patient characteristics, from data logger 54, and then transmits initial setup parameters to device 26. Finally, operator 32 instructs user 22 to operate device 26 between 6 AM and 10 AM each day, during the course of the program.

In a "set baseline" step, user 22 fills in a questionnaire, to provide details of currently-prescribed medications, lifestyle, etc. to remote facility 28. Subsequently, user 22 uses device 26 during ten days of measurements, in which signals and parameters are recorded, corresponding to D2(1) of Table I. After completion of the ten days of measurements, user 22 performs an acute-response test corresponding to T1 of Table I. Device 26 then moves to hold mode until activated by operator 32.

In an initial analysis step, data stored in data logger 54 are transmitted to remote facility 28, where operator 32 reads and analyzes the data. Operator 32 then transfers appropriate parameters CRT to device 26, to enable regular operation of the device.

In a first operation step, user 22 operates device 26 in diagnostic-interventive mode DI1 for one week, after which device 26 moves to hold mode. User 22 transmits data stored in data logger 54 to remote facility 28. Most preferably, the data is transmitted according to configuration 2, described hereinabove. Alternatively, user 22 may contact operator 32 and transmit the data in one of the alternative configurations described above. After the data have been transmitted to operator 32, device 26 returns from hold to its normal working mode.

In a second operation step, user 22 and operator 32 repeat the initial analysis step and the first operation step for four weeks. At the completion of this step, user 22 performs acute-response test T1 described in Table I. User 22 also fills in a second questionnaire.

In a third operation step, user 22 and operator 32 repeat the initial analysis step and the first operation step for between two and four months, while operator 32 checks the data and modifies operation of device 26 as described above.

In a completion step, user 22 completes both questionnaires, and is invited to remote facility 32 to discuss the results of the program.

Figure 9:
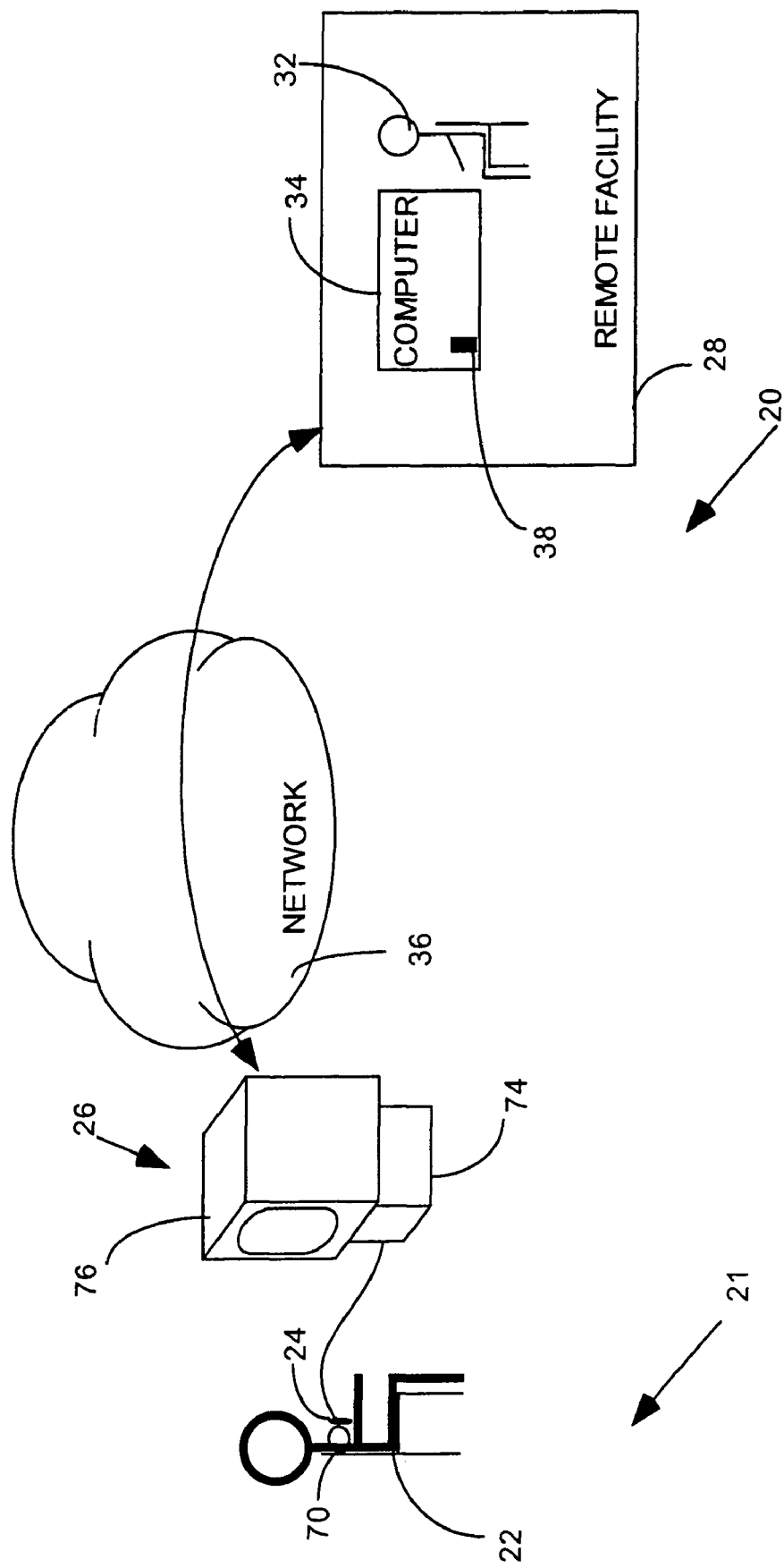
FIG. 9 is a schematic illustration showing how the interventive-diagnostic system of FIG. 1 is applied to an asthmatic child, according to a preferred embodiment of the present invention.

FIG. 9 is a schematic illustration showing how aspects of system 20 are applied in the form of a computer game for user 22, in this case an asthmatic child, according to a preferred embodiment of the present invention. Preferably, the application is for the purpose of enhancing self-control of user 22's breathing when exposed to psychological stressors. Optionally, wheezing is monitored as a benefit-related variable. Alternatively or additionally, respiratory efforts are increased by user 22 by breathing through a resistive load, in order to strengthen and orchestrate the activity of respiratory muscles.

Most preferably, device 26 is implemented in a computer 74 comprising an audiovisual monitor 76, as described hereinabove. Respiration sensor 70, described above with reference to FIG. 7, is coupled to a belt placed around the chest of user 22. Sensor 70 is preferably coupled directly to computer 74, for the purpose of monitoring wheezing as a benefit-related variable. Typically, wheezing is detected by mounting a small microphone (not shown) near user 22's throat. Computer 74 and user 22 are preferably, but not necessarily, in communication with remote facility 28, as described above with reference to configuration 3, so that operator 32 is able to present a dynamic audio-visual pattern, e.g., a game, as a sensory stimulus to user 22. Computer 74 uses input signals from sensor 70 to generate biorhythmic activity parameters corresponding to a respiration rate, an inspiration time, an expiration time, and a graded performance of user 22. Most preferably, the graded performance quantitatively characterizes the breathing of user 22, and comprises, for example, a percentage of time during a session spent executing a prescribed breathing procedure, or other prescribed intervention.

Device 26 also makes measurements of benefit-related parameters derived from pattern classification statistics, respiration rate, inspiration time, and expiration time. Such benefit-related parameters include, for example, a percentage of time spent in a pathological breathing pattern. Device 26 also makes measurements of health status parameters derived from the respiration rate of user 22.

Figure 10:
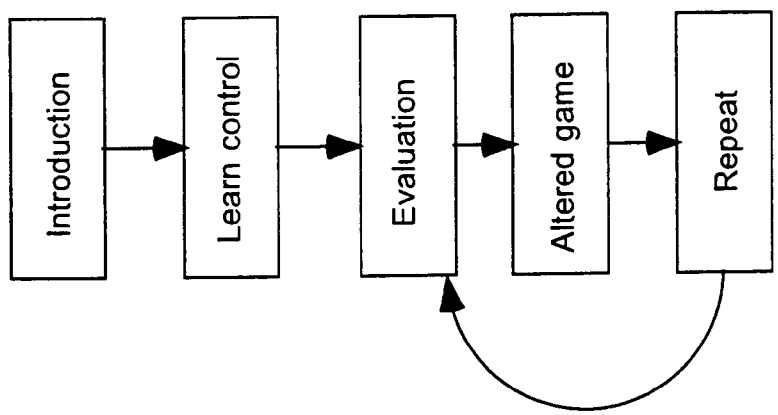
FIG. 10 is a schematic flow chart giving steps involved in a game program to enhance breathing self-control under psychological stressors, for the child described with reference to FIG. 9, according to a preferred embodiment of the present invention.

FIG. 10 is a schematic flow chart showing steps of a game program to enhance breathing self-control during exposure to psychological stressors, for the child described with reference to FIG. 9, according to a preferred embodiment of the present invention. In an introduction step, operator 32 communicates with user 22 and explains rules to be followed during the course of the game program, for example, how to mount sensor 70 correctly. Preferably, the explanations comprise audiovisual explanations and/or questions and answers via an electronic communications program, such as a chat program. The introduction step concludes by user 22 demonstrating to operator 32 that the user is able to correctly mount sensor 70 and operate device 26.

In a "learn control" step, user 22 is given a short course in how to control her/his breathing, typically by slowing down breathing using intervention mode I1, as described above in Table I. Preferably, the stimulus presented to user 22 is in the form of a moving picture on monitor 76, such as an object whose activity responds to the user, and, to encourage proper breathing, can only enter a "high-score" region of the screen when the user's breathing profile closely matches a desired profile. Alternatively or additionally, the size or content of an oxygen bottle carried by an on-screen spaceman, varies in apparent volume or other characteristics responsive to the breathing profile. As described hereinabove, the actual variation of the stimulus is controlled by the output of biorhythmic modifier 44. Preferably, the course includes compiling for user 22 a score representative of how well the course has been followed.

In an evaluation step, diagnosis mode D3, described above in Table II, is applied to user 22, and the results are evaluated by operator 32. At the conclusion of the evaluation, operator 32 transmits parameters CRT to computer 74 so as to alter parameters of the game responsive to the evaluation of the operator.

In an altered game step, user 22 plays the game under the altered conditions. Most preferably, the altered conditions include one or more "adventure" sessions, and one or more "break" sessions. An adventure session typically comprises an intervention mode wherein a psychological stressor is applied, for example I(3) described in Table II. The stressor may be, for some applications, the tension induced in the user by the game's difficulty. A break session comprises an intervention mode wherein no psychological stressor is applied, for example intervention mode I4 described in Table II. During the course of the altered game step, sensitivity to the stressor is measured, e.g., by testing mode T2(1), and the results of the test are used to alter the structure of the game. For example, the percentage of adventure sessions may be increased and the percentage of break sessions may be correspondingly decreased. User 22 most preferably receives scores giving an evaluation of the user's performance during the course of the altered game step.

The game continues by repeating the evaluation step and the altered game step, the repetition being made conditional on user 22 achieving a specific score in the altered game step. Most preferably, each repetition increases the level of difficulty of the game, e.g., by increasing the percentage of time spent in adventure sessions.

In some preferred embodiments of the present invention, a plurality of games, which are similar to the game described with reference to FIG. 10, are operated by a corresponding plurality of users. Most preferably, the users are in communication with each other via network 36, so that respective scores of the users are visible to some or all of the users. Most preferably, operator 32 is also able to see the plurality of scores of the users. Friendly competition or team-work between the users may be encouraged, for the benefit of all.

In some preferred embodiments of the present invention, the game as described with reference to FIG. 10 is operated by user 22 without the intervention of operator 32, optionally under the supervision of an adult. In these embodiments, the functions of operator 32 may alternatively be performed by device 26, whereby a mode and a sequence of program steps are stored respectively in mode storage component 54 and sequencer 56.

It will be understood that whereas preferred embodiments of the present invention have been described generally with respect to a user having a pathology, it is within the scope of the present invention for the user to be generally healthy, and to choose to use aspects of the present invention in order to obtain psychological stress-relief and/or relaxation, or for purposes of muscle re-education, athletic training, or entertainment.

Figure 11:
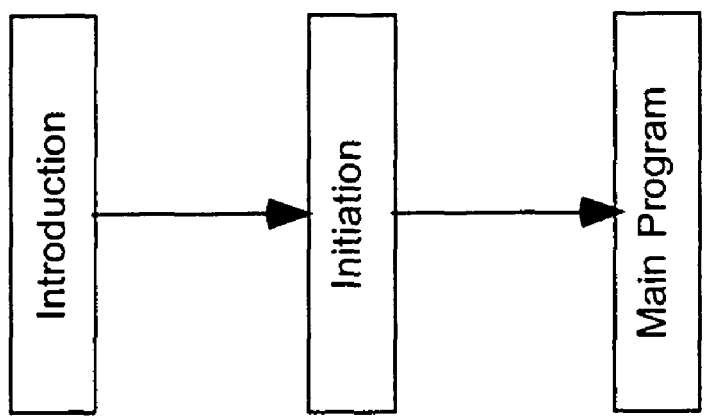
FIG. 11 is a schematic flow chart giving steps involved in a blood pressure treatment program, according to a preferred embodiment of the present invention.

FIG. 11 is a schematic flow chart showing steps involved in a blood pressure treatment program, according to a preferred embodiment of the present invention. An objective of the program is to reduce the blood pressure of user 22 within a period of about 6 weeks. Most preferably, system 20 is set up as described above with reference to FIG. 9, so that user 22 is connected to device 26 and respiration sensor 70. Alternatively, device 26 is implemented as a stand-alone device. Further alternatively, other sensors may additionally be used, such as a photoplethysmography (PPG) sensor, an ECG sensor, or a blood pressure monitor. Depending on the sensors used, benefit-related parameters comprising rate and stability of breathing, state of small blood vessels, heart rate variability, values of pulse wave velocity, and blood pressure are utilized in performing the program. Health status variables used in the program typically comprise blood pressure, heart rate and heart rate variability, and breathing pattern.

In an introduction step, user 22 receives device 26 and appropriate sensors. Operator 32, who is most preferably a physician, introduces user 22 to the program, and provides user 22 with instructions as to how to operate device 26 and the sensors. This step may take place at remote facility 28, or partly at the remote facility and partly at site 21.

In an initiation step, user 22 performs self-training, after which, measurements are made to determine the user's baseline characteristics. At the end of the baseline characterization, user 22 performs various tests. Operator 32 accesses device 26 to download the data generated by the program to date, and analyzes the data. The results of the analysis are then used by operator 32 to set up device 26, for example, including appropriate parameters and a choice of music to be stored in the mode storage component of device 26.

In a main program step, user 22 treats himself for an extended period of time, for example 4 weeks. During this time operator 32 monitors data generated by the treatment. In case of difficulty, operator 32 and user 22 are able to communicate with each other, for example, to provide help to user 22 in performing the treatment. This step is repeated as needed, and during the course of the step, operator 32 modifies the setup of device 26 according to the progress of user 22.

Figure 12:
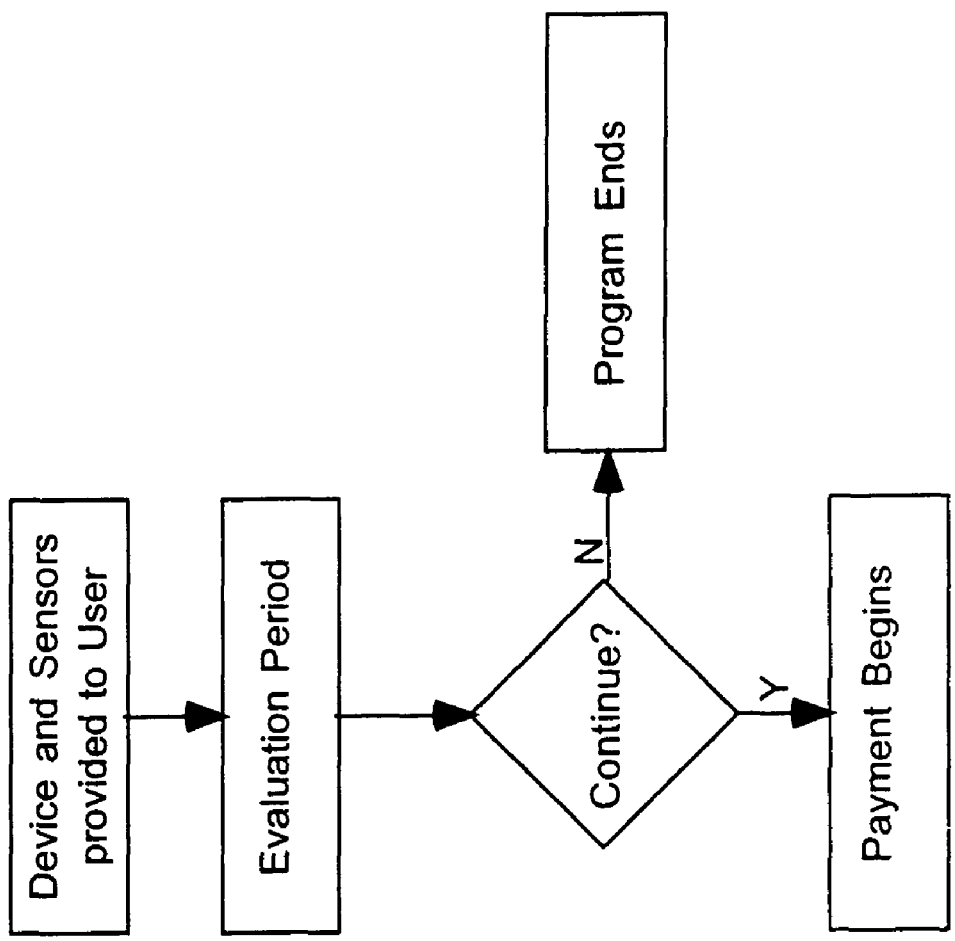
FIG. 12 is a schematic flow chart giving steps involved in a process of providing the interventive-diagnostic system of FIG. 1 to a user, according to a preferred embodiment of the present invention.

FIG. 12 is a schematic flow chart showing steps involved in a process of providing system 20 to user 22, according to a preferred embodiment of the present invention. Device 26 and one or more of sensors 24 and 25 are provided to user 22 from remote facility 28, or from another facility remote from local site 21, so that user 22 is able to transport the device and sensors to the local site, such as the user's home. Alternatively, device 26 is provided to user 22 as a program which can be installed in a computer operated by the user at local site 21. Most preferably, when device 26 and/or the sensors are provided to user 22, the user enters into an agreement with remote facility 28 or with the other remote facility, so as to be able to fully implement interventive-diagnostic system 20, as described hereinabove. Preferably, the agreement provides for user 22 to receive services from remote facility 28, which services comprise facility 28 operating system 20 for an evaluation period without user 22 paying for the services. In the event that user 22 wishes to continue the services after the evaluation period, the user, an insurance company, or another entity pays for the services, for example on a monthly basis. In the event that user 22 does not wish to continue to receive the services, the program is terminated.

It will be understood that it is within the scope of the present invention for an intervention, as described hereinabove, to include use of physical apparatus not specifically mentioned. This apparatus may comprise, for example, substantially any anaerobic or aerobic recreational or therapeutic exercise equipment known in the art. Alternatively or additionally, the apparatus may comprise an airway resistance-generation device, such as a Positive End Expiratory Pressure (PEEP) valve, an inspiratory or expiratory breathing retrainer, or other respiration-manipulation unit. Alternatively, the intervention may be partially or completely free of apparatus, and involve, for example, 15 minutes of walking, pursed-lips breathing, a Valsalva maneuver or aerobic exercise in time-relation with breathing movements (e.g., as applied in Qi-gong), or intentionally-generated breathing patterns, as done in Yoga and zan-zen. In some of these applications, principles of the present invention may be utilized in combination with a medical device already in use by the user, such as a ventilator. The principles may be applied, for example, to wean the user from the ventilator.

Figure 13:
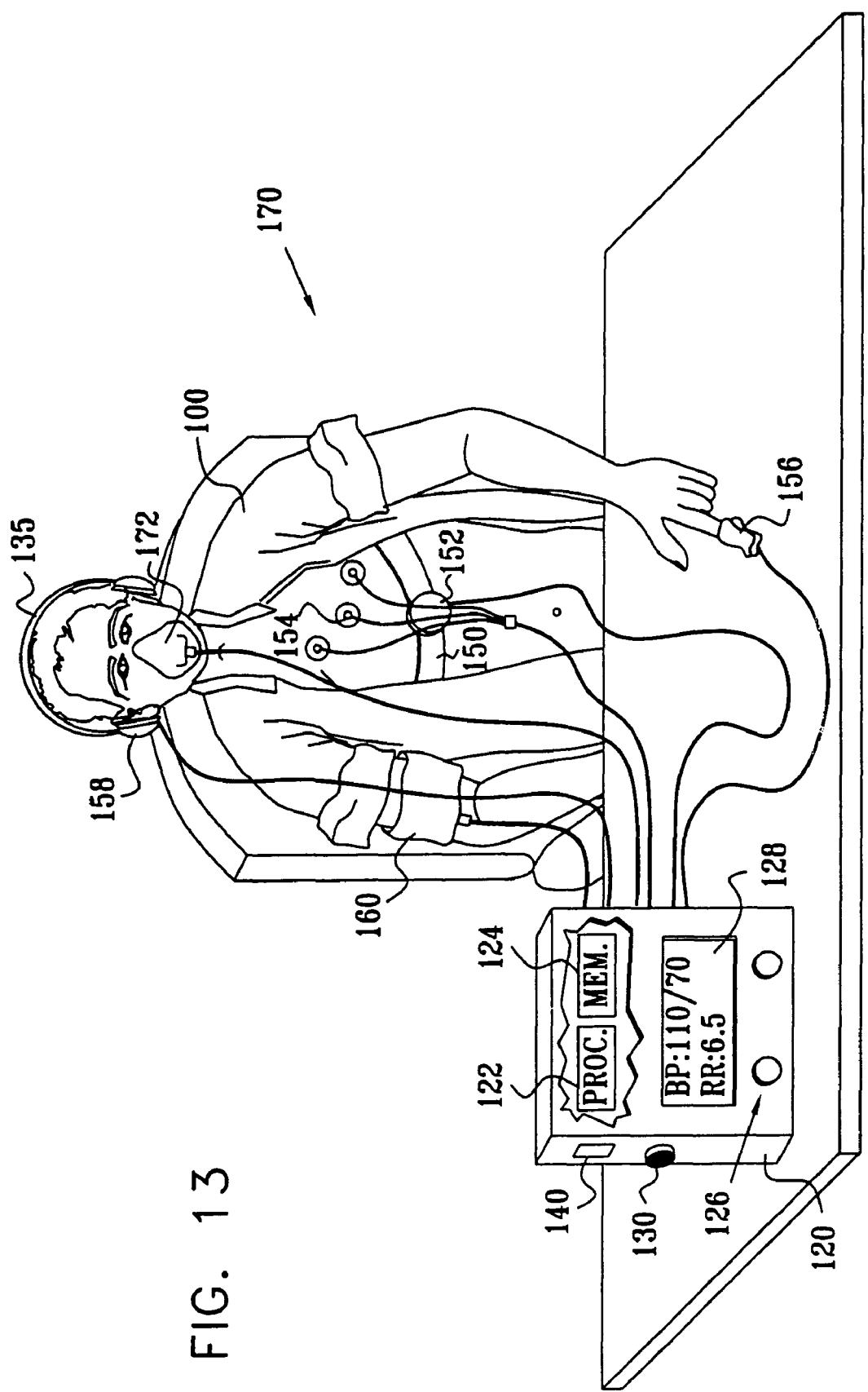
FIGS. 13 and 14 are schematic pictorial illustrations of devices for improving the health of a user, in accordance with respective preferred embodiments of the present invention.

FIG. 13 is a schematic pictorial illustration of a device 120 for improving the health of a user 100, in accordance with a preferred embodiment of the present invention. For many applications, device 120 functions according to protocols substantially similar to those which govern the function of local computing device 26, described hereinabove.

It will be appreciated that although many functions of device 120 are described with respect to the device operating in a stand-alone mode, particular advantages can nevertheless be obtained by transferring data and instructions, through a data port 140 of the device, to and from a remote server, as described hereinabove. Typically, device 120 accesses through the Internet a Web page maintained by the server, and displays on a screen 128 recommendations which are generated by the server or by a case manager who intermittently reviews data sent by device 120 to the server. The server or the case manager preferably analyzes the data to determine the efficacy of the therapy provided by device 120, to change operating settings of the device, and/or to identify the onset of a developing abnormal or dangerous condition of user 100. The data preferably comprise diagnostic variables measured by device 120, as well as data keyed-in by the user. Further preferably, the analysis includes a review of these data, of other treatments administered to the user (e.g., pharmaceutical treatments), as well as of the user's compliance with these treatments. Still further preferably, a report is periodically generated by the server, and is sent to the user's physician and/or to the user. Alternatively or additionally, the user and/or the device prepares the report prior to the user visiting his/her physician.

Device 120 preferably comprises a speaker 130 and/or a headset 135, through which music is played or instructions are given, such that in combination with voluntary action by the user, one or more physiological variables of user 100 may be beneficially modified. Preferably, the music is generated by a processor 122 of the device, in a manner substantially similar to that described hereinabove and in the above-cited patents to the present inventor. Alternatively or additionally, the music is generated in accordance with the methods described hereinbelow with reference to FIG. 16. Further alternatively or additionally, processor 122 drives screen 128 to display graphical patterns, images, or instructions which direct the user to modify an aspect of his respiratory pattern or of another controllable physiological variable. In this case, the material presented on screen 128 is preferably configured to vary in its rhythm, color, or perceived motion in a manner analogous to that produced by the music algorithms described herein and in the patents to the present inventor which are incorporated herein by reference. A keypad 126 is optionally provided to allow user 100 to enter various forms of data, e.g., responses to questions displayed on screen 128.

One or more sensors 170 are preferably coupled to the user's body, and measure physiological variables over which user 100 generally exercises no direct control, i.e., physiological variables typically governed at least in part by the autonomic nervous system. Typically, sensors 170 comprise at least one of the following: a blood pressure cuff 160, a respiration unit 172, photoplethysmography or blood oximetry sensors 156 and 158, and electrocardiographic electrodes 154. For some applications, sensors (not shown) which measure other physiological variables controlled by the autonomic nervous system are alternatively or additionally coupled to convey signals to processor 122.

In addition to sensors 170, at least one other sensor 152 is preferably coupled to convey to processor 122 signals responsive to a physiological variable which is generally under the user's direct control, for example, respiration rate. In a preferred embodiment, sensor 152 is attached to a belt 150 placed around the user's chest, and is adapted to measure the timing and the depth of the inspiratory and expiratory phases of the user's respiration. Suitable sensors and other apparatus and techniques for use with this embodiment of the present invention are described in the present patent application (particularly with reference to FIGS. 17A, 17B, and 17C hereinbelow), in the above-cited patents to Gavish, in U.S. patent application Ser. Nos. 09/101,540 and 09/191,517, and in PCT Patent Publication WO 97/26822, all of which share common inventorship with the present patent application and are incorporated herein by reference.

In a preferred application, processor 122 guides user 100 to change his/her breathing pattern in a way that typically increases tissue oxygenation. This application of the present invention is particularly useful in the treatment of congestive heart failure (CHF), which often causes afflicted patients to demonstrate an abnormal breathing pattern called Cheyne-Stokes respiration, in which periods of hyperventilation are followed by periods of apnea. This breathing pattern leads to a drop in average tissue oxygenation, because excessively-slow breathing does not supply sufficient levels of oxygen to the body, and hyperventilation places a severe load on the patient's already weak heart and does not optimally oxygenate the body. Preferably, musical patterns as described herein include musical or vocal guidance to the user to inhale and to exhale according to a schedule which gradually brings his respiration into a desired, healthy pattern, so as to increase tissue oxygenation. In accordance with a preferred embodiment of the present invention, protocols described in the above-cited articles by Mortara and Bernardi are utilized in applying the techniques described herein, so as to obtain desired increases in tissue oxygenation. The musical or vocal guidance to inhale may include, for example, a flute playing a sequence of notes which generally rises in pitch and/or volume, while the direction to exhale may include cello notes which fall in pitch and/or volume. Alternatively, the user is instructed at the beginning of the session to inhale whenever he hears a flute or a tone having a specified high pitch, and to exhale whenever s/he hears the cello or a tone having a specified low pitch. Preferred protocols for generating the music are described hereinbelow with reference to FIG. 16.

In some applications, sensor 156 conveys to processor 122 signals which are indicative of skin blood volume and/or blood oxygen levels. In response, the processor adjusts rhythmic parameters of the music, so as to direct the user to modify the duration of the inspiratory phase and/or the expiratory phase, and to thereby drive the signals from sensor 156 towards desired values. For example, the inventor has found that programming device 120 to gradually increase the proportion of respiration spent in the expiratory phase, while simultaneously gradually reducing the respiration rate to about six breaths per minute, yields the desired results of significant increases in blood oxygenation and significant decreases in blood pressure in some patients.

In a preferred embodiment, processor 122 stores in a memory 124 of device 120 some or all of the physiological data recorded during a session, as well as parameters of the music or other interventions which were applied during that session. The processor preferably analyzes these data and parameters to determine optimum intervention settings for the user. It is noted that as the health of the user changes (e.g., over the course of days or weeks), these settings may also change, so the optimization process is preferably performed after every session, or in real time during a session.

In a manner analogous to that described hereinabove with respect to blood oxygenation, other autonomic nervous system functions can be monitored and varied using device 120, in accordance with a preferred embodiment of the present invention. For example, decreased heart rate variability is known in the art to be associated with cardiovascular impairment. (See, for example, the above-cited article by La Rovere et al.) To treat this phenomenon, in one application electrocardiographic electrodes 154, blood pressure cuff 160, sensors 156 and/or sensors 158 send signals to processor 122 indicative of the heart rate of user 100, and processor 122 modifies aspects of the music or other intervention so as to increase heart rate variability. It has been shown that slow breathing increases heart rate variability. (See, for example, the above-cited article by Pitzalis et al.)

Alternatively or additionally, device 120 is operated so as to increase the mechanical compliance of the user's blood vessels. This compliance reflects the ability of blood vessels to expand in response to passage therethrough of blood ejected from the heart. Sufficient levels of arterial compliance are known to be important in buffering the pulsatile pattern of the blood pushed at high pressure from the heart, thereby smoothing the flow of blood into the microvasculature. Reduced arterial compliance, by contrast, is associated with improper function of baroreceptors which are used by the body in the feedback systems which control blood pressure. Arterial compliance is known to decrease with increasing age, as well as in many cardiovascular diseases, such as hypertension, congestive heart failure, and atherosclerosis. Moreover, arterial compliance decreases in response to an acute increase in blood pressure, and in response to increased sympathetic nervous activity, e.g., when a person is experiencing mental stress.

Preferably, device 120 increases arterial compliance in a manner generally analogous to that described hereinabove with respect to increasing blood oxygenation. Thus, processor 122 may modify parameters of the music or other intervention presented to the user in order to determine suitable operating parameters which cause signals from one or more of sensors 170 to indicate that arterial compliance is increasing. The inventor has found that many cardiovascular indicators are optimized by causing the respiration rate or another voluntary or involuntary physiological parameter of the user to cycle at approximately 6 repetitions per minute.

Changes in arterial compliance are preferably measured by monitoring changes in the pulse wave velocity corresponding to each beat of the user's heart. Decreases in pulse wave velocity are generally desired, as they are derived from increases in arterial compliance. Changes in the pulse wave velocity are typically measured by calculating the time delay between events corresponding to the same heart beat that are measured at different distances from the heart. For example, processor 122 may measure changes in the time difference between the QRS complex of the electrocardiographic signal measured by electrodes 154 and the onset of a corresponding change in the photoplethysmography signal measured by sensor 156. Alternatively or additionally, the processor determines the difference in time between the detection of a cardiac contraction by sensor 158 on the user's ear, and the detection of the same contraction by sensor 156, coupled to one of the user's fingers.

Preferably, processor 122 sets the musical breathing directions or other applied interventions so as to maximally decrease the pulse wave velocity measurements, while substantially continuously monitoring the user's ability to comfortably adhere to the breathing or other regimen. For example, even if it were determined that an additional marginal decrease in pulse wave velocity could be attained by reducing the respiration rate from six to five breaths per minute, such a reduction would typically not be done if it were also determined that the user would take excessively large breaths at the slower rate and/or overload the heart and respiratory muscles.

For some applications of the present invention, it is desirable to apply an intervention to user 100 at a frequency between about 0.05 Hz and 0.15 Hz, which corresponds to the vasomotor frequency associated with "Mayer waves"—periodic fluctuations in lumen of the smaller blood vessels. For example, the user may be directed to breathe at the vasomotor frequency, or blood pressure cuff 160 may be adapted to cyclically apply pressure to the user's arm at this frequency. Alternatively or additionally, other stimulating apparatus applies to other areas of the user's body cyclic doses of a mechanical input, such as positive or negative air or fluid pressure. Further alternatively or additionally, electrodes 154 or other electrodes, magnets, heating or cooling units, or electromagnetic radiation emitting units placed on, in, or near the user's body, apply or remove at the vasomotor frequency corresponding forms of energy to or from the designated areas of the user's body.

In a given individual, the vasomotor frequency varies over long periods of time, and, the inventor believes, even during short time periods such as a typical 15 minute session when user 100 is interacting with device 120. Preferably, sensor 156, sensor 158, and/or other sensors substantially continuously convey signals to processor 122 which are indicative of a current value of the vasomotor frequency of user 100. It is hypothesized that by closely matching the frequency of application of an intervention to the current value of the vasomotor frequency, device 120 is able to achieve a form of cardiovascular resonance, which induces significant improvements in known indicators of cardiovascular health. (See, for example, the above-cited article by Cook et al.) The intervention may include any of the interventions described herein, such as induced changes in respiration rate, cyclically applied mechanical pressure, heat, cooling, or application of electrical fields, magnetic fields, or various forms of electromagnetic radiation. In a preferred embodiment, one or more of these interventions is applied cyclically at the vasomotor frequency to injured tissue, in order to enhance the healing of the tissue.

For some applications, respiration unit 172 monitors and/or modifies the airway resistance or the mechanical load of the respiratory system of user 100. If appropriate, based on the user's medical condition, respiration unit 172 may cause the user to inhale or exhale against a mechanical load, so as to exercise his/her respiratory muscles and/or to dilate or otherwise affect some of the respiratory passages. Alternatively or additionally, processor 122 directs the user (e.g., via the music) to modify aspects of his/her inspiration and expiration, so as to modulate a measured value of airway resistance or mechanical load, and to thereby improve mechanical or other characteristics of his/her respiratory system. Further alternatively or additionally, in response to blood oxygenation levels monitored by sensor 156, processor 122 actuates electromechanical apparatus (not shown) to change the mechanical load engendered by respiration unit 172 on user 100. In this manner, it is possible to maximize the user's endurance, while avoiding overloading the user's heart. Suitable forms of breathing maneuvers and other exercises are known in the art, and include those performed in hospitals before and after abdominal and thoracic surgery, as well as those performed by patients with chronic obstructive pulmonary disease.

In cases where a patient has chronic obstructive pulmonary disease (COPD), it is known in the art to instruct the patient to increase his respiratory endurance by breathing 15 breaths per minute through an inspiratory load, while spending 60% of each respiratory cycle inhaling, and 40% of the cycle exhaling. Because of the high levels of mental concentration and physical effort that such an exercise requires, and because of the relatively boring nature of the task, most patients have difficulty following such a regimen, and even dedicated patients tend to stop performing the exercise except under the direct supervision of a healthcare worker.

In preferred embodiments of the present invention, by contrast, the mental effort is substantially eliminated, because user 100 need only listen to the music and breathe in accordance with its rhythm and pattern. In addition, by being responsive in real-time to the user's current breathing pattern, this embodiment provides significantly more functionality than would, for example, an "inhalation indicator light," which simply has a 60% duty cycle and turns on 15 times per minute. Processor 122, by contrast, typically gradually changes the user's breathing pattern from its initial measured state (e.g., 8 breaths per minute, 30% inhale and 70% exhale) to the desired final state. Preferably, this change is caused by guiding the user's respiration through a two-dimensional parameter space defined by {[Breathing Rate], [Inspiration: Expiration Ratio]}. Typically, the processor guides the user's respiration from a point in the space representing the initial state, along the shortest path through the space, to a point in the space representing the desired final state. It is noted that, unlike the above-mentioned blinking light or a pre-recorded cassette, the processor preferably tracks the user's ability to breathe at each of the points along this path, and does not direct him/her to push harder towards a later goal if s/he has not successfully attained the current respiration requirement.

It is known that the respiratory system of some patients is slow to recover following surgery, and that other patients take days or weeks to successfully wean themselves from a mechanical ventilator. Therefore, some applications of the present invention are directed towards using the apparatus and methods described herein, mutatis mutandis, to gradually retrain ventilator-dependent or post-surgery patients in proper breathing techniques. Many mechanical ventilators for use with alert patients are triggered to support the patients' breathing efforts, rather than to dictate the timing and depth of every breath. Because some embodiments of the present invention utilize the user's voluntary control over his/her own breathing, it is preferable to use such triggered ventilators when employing device 120 to wean ventilator-dependent patients.

Figure 14:
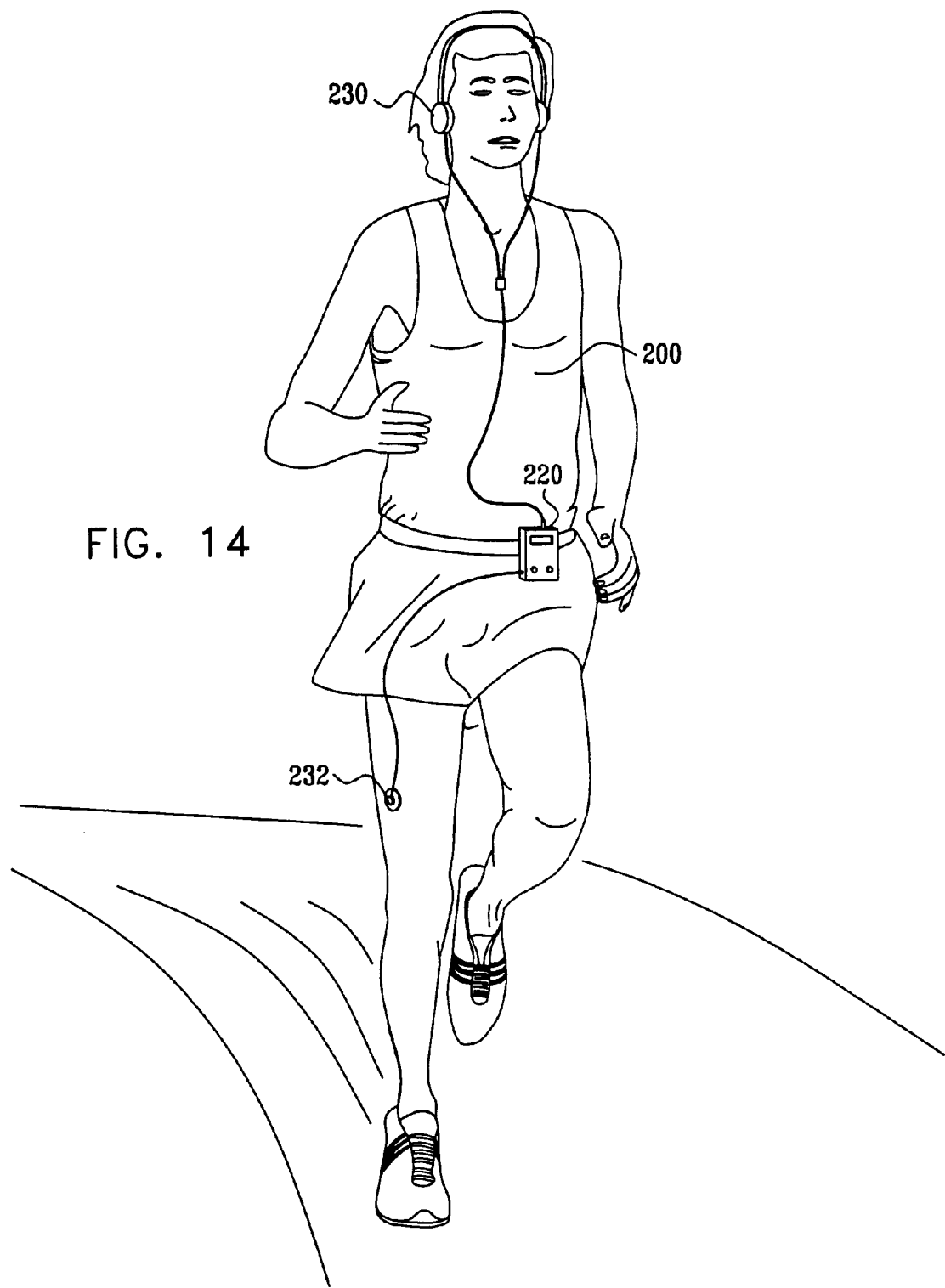

FIG. 14 is a schematic pictorial illustration of a device 220 for improving the health of a user 200, in accordance with a preferred embodiment of the present invention. User 200 is shown in FIG. 14 as a runner, but may alternatively be a weight-lifter, swimmer, dancer, or substantially anyone who performs a repetitive and/or rhythmic activity and is able to modify a timing characteristic of the activity responsive to directions from device 220. The device is preferably configured in a fashion which is generally similar to device 100, described hereinabove with reference to FIG. 13. Although for some applications, device 200 is coupled to a plurality of sensors applied to different portions of the user's body (as shown in FIG. 13), device 200 is preferably adapted to be coupled to a small number of sensing and/or actuating elements, such as, for example, a single element 232.

Typically, element 232 performs sensing functions, e.g., sensing of motion of one of the user's legs and photoplethysmographic sensing. Alternatively or additionally, element 232 senses other physiological variables of user 200, and is placed at an appropriate location in or on the user's body so as to optimally perform this function. In a preferred embodiment, element 232 additionally comprises an actuating unit, which is driven by device 220 to apply, for example, a fast mechanical vibration to one of the user's legs to tell him that that leg should be at a particular phase of the running cycle.

In a preferred application of this embodiment, device 220 continuously monitors the heart rate of user 200, and triggers element 232 to apply the mechanical vibration or other stimulus to the user, so as to direct the user to change the pace of his running in accordance therewith, such that the heart rate is maintained within predetermined limits. Optionally, these limits can be set to vary during the course of a 20 minute exercise session, e.g., 80-100 beats/minute during the first five minutes, 100-140 beats/minute during the second five minute period, 140-180 beats/minute during the third five minute period, and 80-100 beats/minute during the final five minute period.

In addition to or instead of the mechanical vibration, a headset 230 may be driven by device 220 to play music in which a readily-perceived aspect of the rhythm of the music, such as the downbeat of each measure, is timed to occur at a time when it is desired that the user's left foot strikes the ground. Optionally, the headset includes photoplethysmographic or other sensing capabilities. People who have exercised while listening to powerfully-rhythmic music know the strong entraining effect of listening to their favorite music while running or performing other types of exercise. Consciously or unconsciously, the body exerts itself to keep up with the rhythm of the music. Yet, inevitably, exercise performed to the rhythm of pre-recorded music is sub-optimal, because either (a) the music is somewhat slower than that which is appropriate for the current stage in the person's exercise, and thus does not cause him to work hard enough, or (b) the music is somewhat faster than is appropriate, or does not slow down when the person starts to run up a steep hill, so the heart rate increases beyond the desired range. Thus, pre-recorded music, no matter how energetic and inspiring, does not give a listener an optimal work-out. By contrast, music algorithms running in device 220 are preferably continuously able to increase or decrease parameters of the music (e.g., the music's volume or tempo) as appropriate, responsive to changes in the user's heart rate or to changes in other physiological variables. For example, the tempo may be decreased if measured electrocardiographic and/or breathing patterns indicate that the user's body is working too hard, e.g., if it has started metabolizing energy sources in an inefficient manner.

In a preferred embodiment, device 220 utilizes stereo spatial effects to enhance the entrainment of the user's running to the music. For example, the music may include a drum beat in the user's left ear each time his left foot is supposed to push off the ground, and a drum beat in the user's right ear each time his right foot is supposed to push off the ground. Alternatively, three-dimensional spatial effects are employed by device 200, e.g., to present an instrumental sound in the user's left (/right) ear, which sounds like it is moving from the user's back-left (/right) to his front-left (/right), in correspondence to desired motion of the user's left (/right) leg. Similarly, for some applications, device 120 (FIG. 13) generates sounds, through a headset or through external speakers, which are perceived by the user as coming from above him during the inspiratory phase and from below during the expiratory phase. While many suitable techniques for generating three-dimensional sound are known in the art in general, some preferred methods are described in the above-cited article by Begault.

Figure 15A:
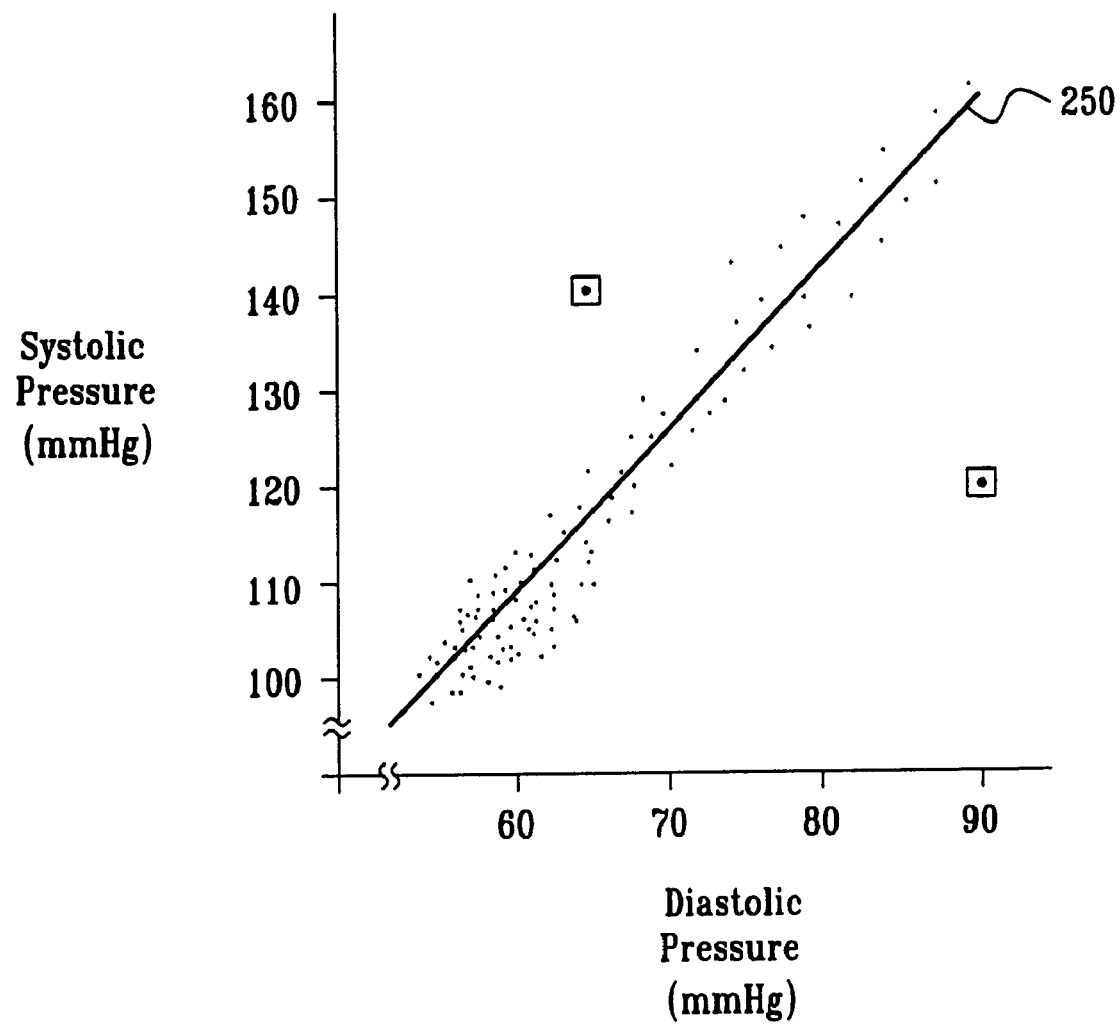
FIGS. 15A and 15B are graphs, schematically illustrating fictitious blood pressure data taken from the user shown in FIG. 13, in accordance with respective preferred embodiments of the present invention.

Reference is now made to FIGS. 13 and 15A. FIG. 15A is a graph, schematically illustrating fictitious blood pressure data of user 100, as recorded by device 120 during one or more sessions, in accordance with a preferred embodiment of the present invention. It is known in the art that self-administered blood pressure measurements made outside of a healthcare facility are often inaccurate and/or inconsistent, due to improper placement of the blood pressure cuff, patient inexperience, or highly-variable measurements conditions.

For example, two significantly-different blood pressure measurements may be made on successive days at exactly 9:00 AM, but may only reflect the fact that on the second day, the user had just finished carrying groceries up a flight of steps. It is thus appreciated that blood pressure measurements for a particular user may vary substantially in successive measurements made during a single day or over many days or weeks. The inventor has found, however, that despite the large variation in blood pressure (e.g., from 110/70 to 160/90), there is a strong and typically linear correlation between the diastolic and the systolic measurements, as is shown in FIG. 15A. Some aspects of this correlation are described in the above-cited abstract, entitled, "Repeated blood pressure measurements may probe directly an arterial property."

Preferably, processor 122 calculates a regression line 250, $$\text{Systolic}=K_1*\text{Diastolic}+K_2,$$

or another statistical relationship which describes the general locations of a substantial number of the points in FIG. 15A. If in a subsequent blood pressure measurement, a systolic-diastolic pair substantially deviate from the regression line (e.g., by greater than two standard deviations along the X-axis, Y-axis, or perpendicularly to the regression line), then processor 122 identifies the systolic-diastolic pair as being an outlier, and automatically actuates blood pressure cuff 160 (FIG. 13) to make another blood pressure measurement. Two such outlier measurements are marked by squares in FIG. 15A. Preferably, blood pressure taken over a representative period are transmitted through data port 140 to a remote server, and the remote server prepares a report for presentation to the user or to his/her physician. Alternatively, the user prints the report and brings it to the physician at the next visit. Further preferably, the report does not contain the blood pressure measurements that were considered outliers. Alternatively, all of the measurements are presented, and a square or other marker is placed around outliers. Preferably, the report contains a summary as well as detailed information, such that the information therein can be quickly and easily read by a medical professional.

In addition to or instead of the statistical analysis just described, processor 122 preferably compares two successive blood pressure measurements made during a relatively short time period (e.g., less than 15 minutes), and automatically initiates a third blood pressure measurement if a function of the disparity between the first two measurements is greater than a threshold. According to one preferred protocol, the systolic (or diastolic) pressure $X_1$ recorded at the first time is analyzed in combination with the systolic (or diastolic) pressure $X_2$ measured at the second time so as to evaluate the following inequality:

$$2*|X_1-X_2|/|X_1+X_2|<0.1$$

If the inequality is true, then any disparity between the two measurements is not considered sufficiently large to label one or the other as suspect. In the event that the inequality is found to be false, however, the processor actuates blood pressure cuff 160 to make a third blood pressure measurement. Preferably, this third measurement is analyzed in combination with the second measurement, to determine whether the disparity therebetween is greater than the threshold. Alternatively, all three measurements are evaluated to determine whether two of them are sufficiently close to each other, and the remaining measurement diverges from the two close measurements. In this case, both close measurements are typically recorded, or the mean of the two close measurements is recorded. Alternatively or additionally, other methods are employed to eliminate spurious blood pressure measurements. This process may continue until the inequality is satisfied, or until indications are found that repeated measurements will not lead to a reliable result, in which case the user is referred to technical assistance (e.g., at the remote server).

Preferably, blood pressure measurements which are not found to be spurious are analyzed over a time period, typically ranging from days to months, so as to determine whether a parameter of the blood pressure measurements changes in a statistically-significant manner during the time period. For example, the systolic and diastolic blood pressure may be monitored to determine whether they demonstrate a statistically-significant drop over a three month period. Preferably, in its optimization of the parameters of an intervention strategy, processor 120 utilizes forms of statistical analysis that are described herein or that would be obvious to a person skilled in the art upon reading this disclosure. Thus, in a sample case treating hypertension, during three consecutive three month periods P1, P2, and P3, having respective intervention protocols I1, I2, and I3, the user's mean systolic blood pressure may be found to be 160, 147, and 142, respectively. Prior art strategies, which typically include drugs, exercise, and/or relaxation techniques, would tend to favor intervention I3, because it yielded the lowest mean systolic blood pressure. According to this embodiment of the present invention, however, device 120 is able to determine the statistical significance of the differences between the results generated by each of the intervention protocols, and in some circumstances would choose intervention I2 as the optimum, rather than I3. This decision by processor 122 would occur in circumstances in which, for example, the mean systolic blood pressure due to intervention I3 is not significantly smaller ($p<0.05$) than that due to intervention I1, while the blood pressure due to intervention I2 is significantly smaller than that due to intervention I1.

It is the inventor's belief that there are no satisfactory methods or apparatus known in the art which accurately and reliably monitor the effect of different intervention strategies on an the blood pressure of an ambulatory patient, because self-administered blood pressure measurements are so frequently flawed, as described hereinabove, and because the costs associated with sufficiently frequent, professionally-administered blood pressure tests are prohibitive for most of the population. This embodiment of the present invention, by contrast, preferably utilizes: (a) statistical analysis of blood pressure data derived from self-administered blood pressure measurements, often including (b) the identification and rejection of a large number of spurious measurements, which result from improper use of the blood pressure apparatus, so as to enable (c) reliable comparisons of the results of various intervention protocols, based upon which processor 122 can initiate (d) automated optimization of the intervention strategy.

Figure 15B:
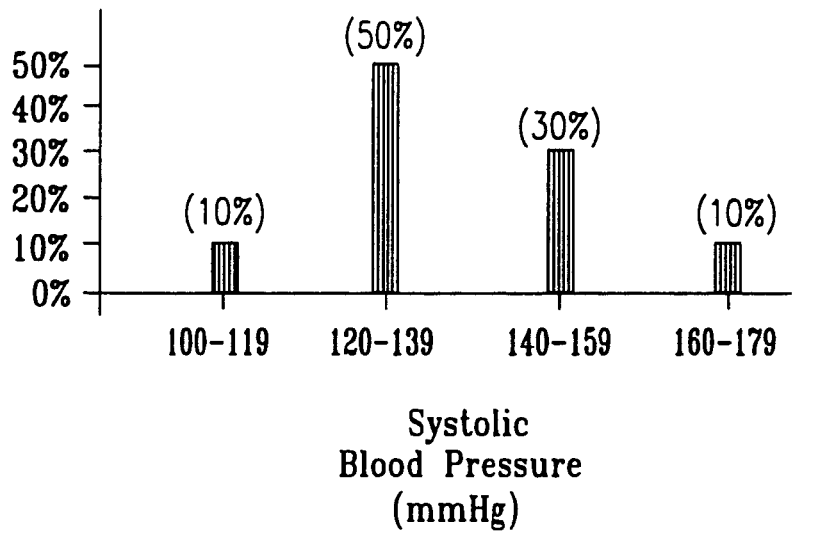
Figure 15B:
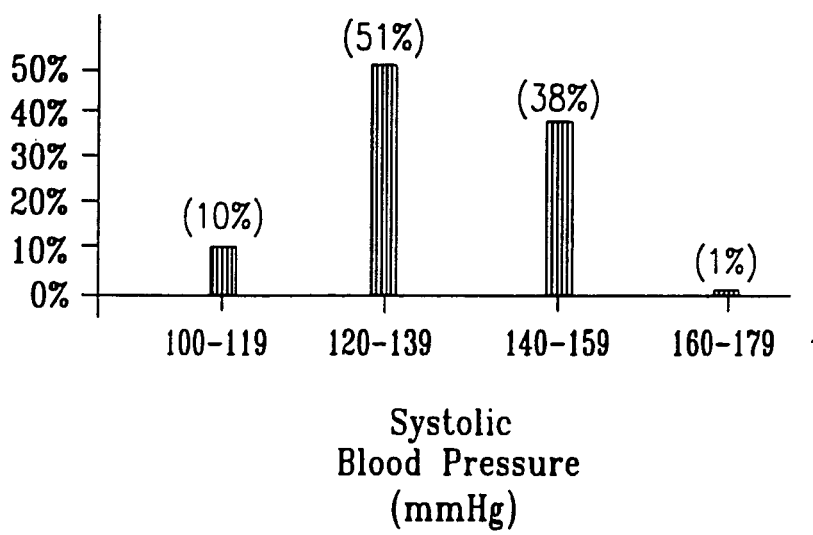

FIG. 15B is a histogram, schematically illustrating fictitious blood pressure data, as recorded by device 120 during two time periods P1 and P2, in accordance with a preferred embodiment of the present invention. It is the inventor's belief that the frequent measurements of blood pressure provided by these embodiments of the present invention yield an additional benefit which is generally not realized using methods and apparatus known in the art. In particular, these embodiments allow processor 122 and/or the user's physician to learn important information based on the distribution of blood pressure measurements (and/or other physiological measurements) taken during the various time periods in which the user operates device 120.

For example, as shown in FIG. 15B, processor 122 or the remote server may generate two histograms showing, during respective time periods, the percentage of systolic blood pressure measurements that were in each of the following ranges: 100-119, 120-139, 140-159, and 160-179. The excessively-high risk of stroke and other cardiovascular diseases known to be associated with systolic pressure above 160 mm Hg suggests to the inventor that a significant reduction of blood pressure in this range alone may contribute considerably to the user's health, even if the mean blood pressure is substantially unaffected. The inventor believes that even if the mean systolic blood pressure value does not change significantly during two or more consecutive time periods, diagnostically-useful information may be obtained by analyzing shifts in the histogram over time.

In particular, it is hypothesized that modifying the intervention protocol so as to reduce the occurrence of systolic blood pressure measurements in the right-most column of the histogram (i.e., systolic readings between 160 and 179) may be even more important than reducing the mean systolic blood pressure. This hypothesis is based on the inventor's understanding that in some patients, a substantial portion of the negative effect of hypertension is caused by the intermittent time periods in which the blood pressure is at its highest values. Therefore, even if there were to be a rightward shift of the histogram at the lower blood pressure levels, which would ostensibly be a negative result of the intervention, this would nevertheless be offset by a leftward shift at higher blood pressure levels. It is noted that in clinical trials using embodiments of the present invention, therapies such as those described herein produce desired leftward shifts in the histogram both at higher and at lower blood pressures.

Figure 16:
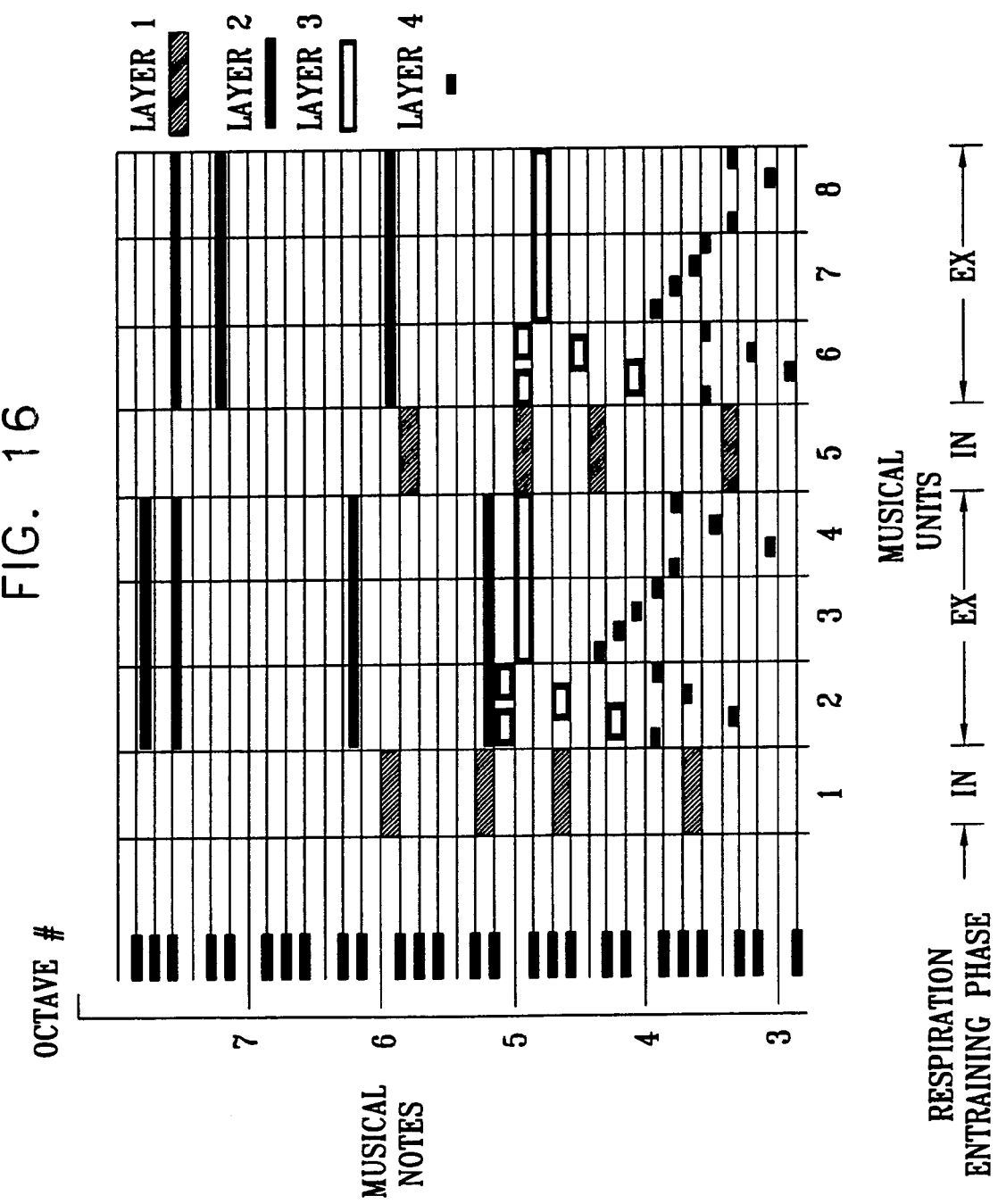
FIG. 16 is a musical composition map, generated in accordance with a preferred embodiment of the present invention.

FIG. 16 is a sample musical composition map, in accordance with a preferred embodiment of the present invention. The vertical (Y) axis shows musical notes, which are represented by piano keys extending from octave 3 to octave 7, and which are preferably coded according to the Musical Instrument Digital Interface (MIDI) protocol or another suitable protocol. Individual musical notes in the composition are represented by segments parallel to the horizontal (X) axis, the length of each segment corresponding to the duration of the respective note (e.g., whole, half, or quarter notes). The X-axis is divided into "musical units," which generally correspond to the measures of standard musical terminology. Each musical note is defined according to standard MIDI notation, as being played by a specified musical instrument, and belonging to a specified "layer" of the output. Since the instruments are synthesized sounds, many sound parameters (such as tempo, overall volume, the volume of each individual layer, and envelope parameters, such as attack rate, decay rate, and echo) can be controlled using standard MIDI commands or other commands which control sound synthesizers.

The example shown in FIG. 16 includes two periods of music, each lasting for four musical units—musical units 1-4 and 5-8. Musical units 1 and 5 correspond to the inspiration phase, while units 2-4 and 6-8 correspond to expiration. Thus, FIG. 16 shows musical patterns corresponding to two complete respiratory cycles.

Unlike music composition software known in the art, music generated according to some preferred embodiments of the present invention is characterized by the music being synchronized with respect to a biorhythmic signal—either to match the biorhythmic signal, or, if the signal is too fast or too slow, to go slightly slower or faster than the signal, respectively. Moreover, according to some preferred embodiments of the present invention, the selection of which particular layers are to have their sound output at any given time is also determined responsive to the biorhythmic signal. For example, if the signal is fast, e.g., corresponding to breathing at 15 breaths per minute, then preferably a small number of layers will be played, or, alternatively, layers having slower notes will be played at the fast tempo corresponding to the respiration rate. In this way, a reasonable, pleasant number of notes will be played during each phase of respiration. However, as the user's respiration is guided by the music to slow down, for example, to 6 breaths per minute, the same set of layers would sound boring, because the total number of notes played during a given time period would be too low. Therefore, as the user's respiration rate decreases, new layers are preferably turned on, which would cause the output of a reasonable number of notes per unit of time.

More specifically, in order to entrain the user's breathing, a basic melody is preferably played in one of the layers, which can be easily identified by almost all users as corresponding to a particular phase of respiration. On top of the basic melody, additional layers are typically added to make the music more interesting, to the extent required by the current breathing rate, as described hereinabove. For example, during the inspiratory phase, the user's respiratory muscles need to develop forces so as to draw in air. This period may be represented by a horn (layer #1), while expiration, which involves an effortless and passive recoil of the rib cage, may be represented by the relaxing music of a flute (layer #2). Typically, the basic melody corresponding to this breathing includes musical cords, played continuously by the appropriate instrument during each phase, as shown in FIG. 16. When either expiration or inspiration extends for more than about two seconds, simple cords like these sound relatively boring. In particular, the ratio of the duration of expiration to inspiration is typically greater than or equal to one, and is guided to increase as breathing becomes slower. Therefore, in order to keep the user interested in the breathing exercise, a third layer having guitar sounds is added to the first two layers (horn and flute) when the duration of the expiratory phase increases above a predetermined threshold. As the duration of the expiratory phase continues to increase, and crosses a second, higher threshold, the guitar layer is silenced, and replaced by a fourth layer (e.g., piano), which has a larger number of musical notes. Alternatively, all four layers play simultaneously when the expiratory phase is particularly long.

The inventor has found that in some applications, up to four layers are typically needed in order to create music that sounds pleasant, so as to entrain breathing in the range of 3 to 30 breaths per minute. The specific choice of instrument(s) to include in each layer depends on the style of musical composition, as well as how it is perceived at different breathing rates and inspiration/expiration ratios. Unlike standard music composition theory known in the art, music as generated by some embodiments of the present invention is somewhat more flexible in its use of tempo and rhythm, even though typical listeners do not generally perceive the difference between the music generated by device 120 and, for example, traditional easy-listening music.

In particular, music generation as practiced by these embodiments of the present invention differs from standard computer music composition (or human music composition) in that physiological rhythms are not usually related by integer multiples of durations, as will be described, whereas, for example, Western music principles essentially require music to have a strictly-regulated rhythmic structure. The inventor has found that although unguided human respiration may have Expiration:Inspiration (E:I) ratios having any real value from 0.50 to 4.0, people do not enjoy music in which, for example, the duration of one measure is 1.4 times the duration of the following measure. Therefore, for example, if it is desired to change the E:I ratio from 1:2 to 4:1, the music typically does not transition the user smoothly through the E:I ratios {4:8, 4:7.8, 4:7.6, ..., 4:1.2, 4:1}, as might be appropriate for a respiration unit which simply employs a blinking light. Instead, music is preferably generated whose basic musical units (e.g., measures) nearly or exactly correspond to a sequence of integer E:I ratios that govern the user's inspiration and expiration, such as (in order): 1:2, 2:3, 3:4, 1:1, 4:3, 3:2, 2:1, 3:1, and 4:1. It is noted that the inspiration or expiration phases would therefore have durations which are integer multiples of a base duration. Alternatively, a simpler set of ratios are used, such as 1:2, 1:1, 2:1, 3:1, and 4:1.

For some applications, it is desirable to elongate slightly the length of one of the respiratory phases, typically, the expiration phase. For example, to achieve respiration which is 70% expiration and 30% inspiration, a musical composition written for an E:I ratio of 2:1 may be played, but the expiration phase is extended by a substantially-unnoticed 16%, so as to produce the desired respiration timing. The expiration phase is typically extended either by slowing down the tempo of the notes therein, or by extending the durations of some or all of the notes.

Preferably, although not necessarily, a set of pre-written musical compositions is stored in memory 124 (FIG. 13), corresponding to each integer ratio which may be used to guide the breathing of user 100. For example, memory 124 may contain one or more compositions corresponding to each of the ratios {i:j}, where i and j range from 1 to 4. Alternatively, substantially all of the music is written according to a 4:1 structure, but the notes are composed such that that segments of various lengths may be removed at the end of each musical unit, so as to generate other integer ratios (e.g., 3:1, 2:1, 1:1), and such that the music still sounds pleasant.

Although music for entraining breathing is described hereinabove as including two phases, it will be appreciated by persons skilled in the art that the music may similarly include other numbers of phases, as appropriate. For example, user 100 may be guided towards breathing according to a 1:2:1:3 pattern, corresponding to inspiration, breath holding (widely used in Yoga), expiration, and post-expiratory pause (rest state).

In a preferred embodiment, the volume of one or more of the layers is modulated responsive to a respiration characteristic (e.g., inhalation depth, or force), so as to direct the user to change the characteristic, or simply to enhance the user's connection to the music by reflecting therein the respiration characteristic.

Alternatively or additionally, parameters of the sound by each of the musical instruments may be varied to increase the user's enjoyment. For example, during slow breathing, people tend to prefer to hear sound patterns that have smoother structures than during fast breathing and/or aerobic exercise.

Further alternatively or additionally, random musical patterns and/or digitized natural sounds (e.g., sounds of the ocean, rain, or wind) are added as a decoration layer, especially for applications which direct the user into very slow breathing patterns. The inventor has found that during very slow breathing, it is desirable to remove the user's focus from temporal structures, particularly during expiration.

Still further alternatively or additionally, the remote server maintains a musical library, to enable the user to download appropriate music and/or music-generating patterns from the Internet into device 120. Often, as a user's health improves, the music protocols which were initially stored in the device are no longer optimal, so the user downloads the new protocols, by means of which music is generated that is more suitable for his new breathing training.

Figure 17A:
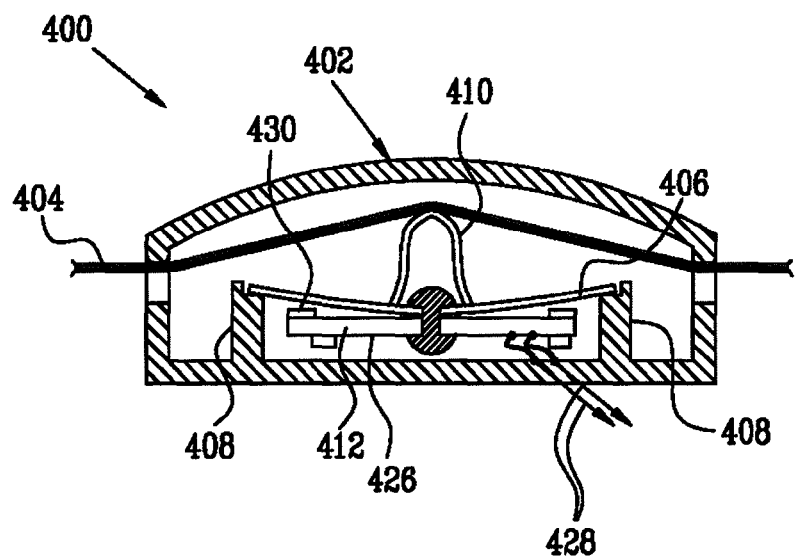
FIGS. 17A, 17B, and 17C are schematic illustrations showing different aspects of a capacitive sensor, in accordance with a preferred embodiment of the present invention.
Figure 17B:
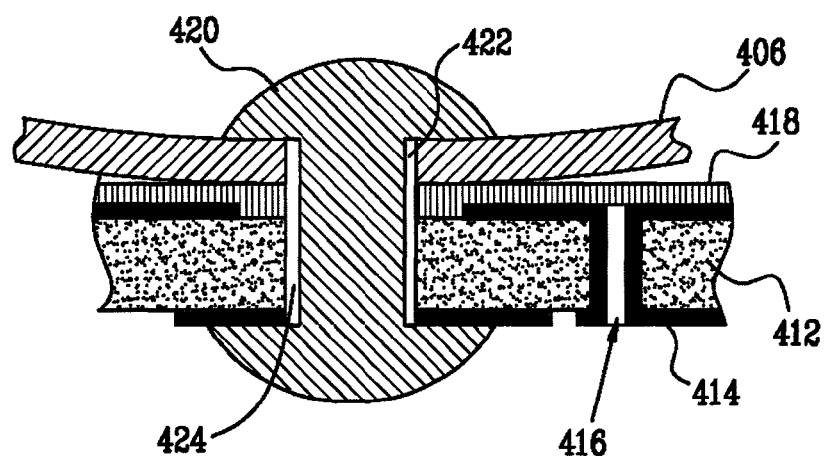
Figure 17C:
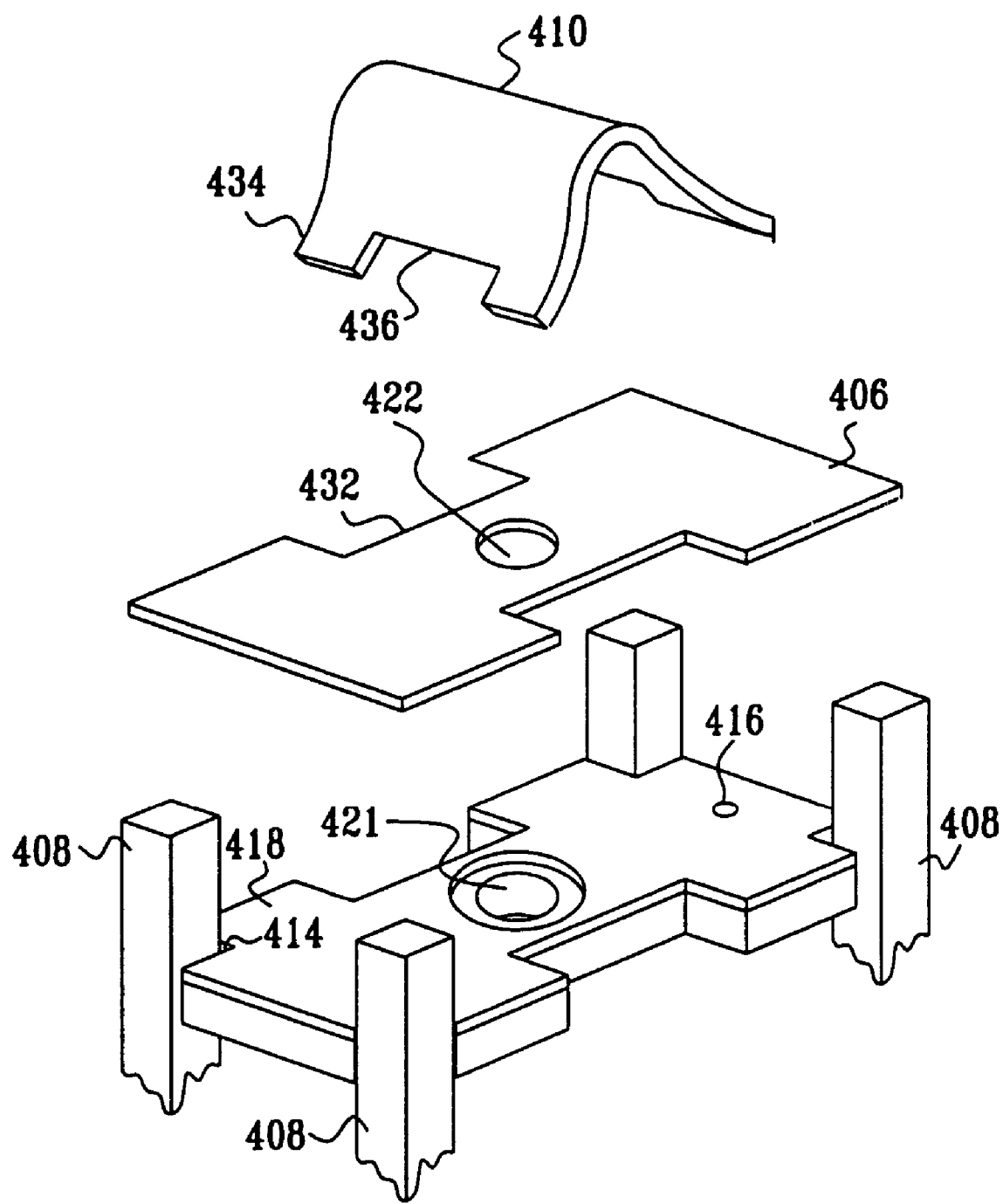

FIGS. 17A, 17B, and 17C are schematic illustrations of a stress-detecting device 400, for sensing respiration of a user, in accordance with a preferred embodiment of the present invention. FIG. 17A is a cross-sectional view of the whole device, FIG. 17B is a magnified view of a central region of FIG. 17A, and FIG. 17C is a perspective view of a preferred implementation of device 400. For some applications, device 400 is used as part of the sensor structures described in U.S. Pat. No. 5,423,328. It is noted that FIG. 17C shows device 400 according to an embodiment which is appropriate for mass production and is relatively inexpensive to build.

Stress-detecting device 400 preferably includes a biorhythmic activity sensor 402, slidably disposed on a belt 404 worn by the user. Belt 404 is preferably elastic and/or stretchable along at least a potion of its length. Output signals of sensor 402 are preferably transferred to monitoring apparatus such as device 120 (FIG. 13), either by wired or wireless communication. Alternatively, device 400 may be provided with a display (not shown), as described in U.S. Pat. No. 5,423,328.

Device 400 preferably comprises a deformable plate 406, constructed of an elastic material, which is conductive on at least one large surface thereof. The deformable plate is supported from below by plate supporters 408. In order to minimize friction, the position of deformable plate 406 is preferably not fixed by plate supporters 408. The stress of belt 404 is exerted on deformable plate 406 by means of a bridge 410, which may be an integral part of the deformable plate 406 or separate therefrom, and is preferably made of a low-friction material to allow the belt to slide easily thereon. A counter plate 412, preferably made of a rigid material, is also conductive on at least one large surface thereof. Typically, counter plate 412 is made of a rigid plastic insulating material used in manufacturing printed circuit (PC) boards, where a surface thereof which is closer to deformable plate 406 has printed thereon a conductive layer 414. This layer preferably extends to the opposite surface of counter plate 412 by means of a coated through-hole 416, as is well known in the art of manufacturing PC boards. As shown in FIG. 17B, conductive layer 414 is preferably covered by an insulating layer 418, which is a standard procedure in the manufacture of PC boards.

Together, conductive layer 414 and the conductive surface of deformable plate 406 effectively create the plates of a capacitor. The gap between these plates is preferably filled with an insulating, dielectric material and air, with properties of the insulating material selected depending on the expected extent of deformation of deformable plate 406. It is noted that, unlike most capacitive sensors known in the art which produce changes in capacitance responsive to deformation of an elastic dielectric, the capacitance of device 400 is substantially not dependent on the properties of the material which fills the gap.

Deformable plate 406 and counter plate 412 are preferably compressed and fixed by a fixing pin 420, widely used for that purpose in the mass production of PC boards. Fixing pin 420 passes through holes 422 and 424 in deformable plate 406 and counter plate 412, respectively, while creating electrical contact with the conductive surface of deformable plate 406 and a conducting surface preferably printed on the side of counter plate 412 opposite to conductive layer 414.

In a preferred embodiment, counter plate 412 forms a base for electronic components and printed circuits 426, which are typically used to convey a signal indicative of the capacitance engendered by the proximity of conductive layer 414 and the conductive surface of deformable plate 406. As appropriate, the signals may be transmitted wirelessly or via a cable 428 to another device. Preferably, cable 428 is configured in a manner so as not to mechanically load counter plate 412. Stress-detecting device 400 is typically, but not necessarily, powered by a battery or is coupled to an external power source via cable 428.

Depending on the details of the construction of stress-detecting device 400, deformable plate 406 and counter plate 412 are typically close to each other and relatively loose when no stress is applied by belt 404 on bridge 410. Therefore, it is generally advantageous in these cases to incorporate insulating protrusions 430 into device 400, so as to control the position and/or relative motion of deformable plate 406 and counter plate 412 under no-stress conditions.

Preferably, bridge 410 is somewhat elastic, and may be inserted into square grooves 432 of deformable plate 406 (FIG. 17C), so that legs 434 of the bridge slightly press deformable plate 406 from the counter plate 412, which force is counteracted by a base 436 of the bridge. Preferably, electric contact between fixing pin 420 and conductive layer 414 is avoided by discontinuing conductive layer 414 in the vicinity of hole 424 (as shown in FIG. 17C).

Advantageously, stress-detecting device 400 displays a relatively large capacitance at no-stress, due to the small gap between deformable plate 406 and counter plate 412, which capacitance sharply decays as the stress increases. By selecting stainless steel as a material for deformable plate 406, the range of stresses in the steel generated by breathing movements yield small deformations of plate 406, which nevertheless produce substantial changes in the capacitance of device 400. Thus, the stress-detecting device is highly sensitive to even small breathing motions. By using the changes in capacitance to drive an oscillator, as will be understood by a person skilled in the art, a 5-fold change in frequency can be achieved for a 2 cm$^2$ area of deformable plate 406, in typical conditions for monitoring breathing movements. The inventor has found that stress-detecting device 400 is able to achieve a reproducible, nearly linear, frequency-to-stress relation.

It will be appreciated by persons skilled in the art that the present invention is not limited to what has been particularly shown and described hereinabove. Rather, the scope of the present invention includes both combinations and subcombinations of the various features described hereinabove and in the above-cited patents, patent applications, and articles, as well as variations and modifications thereof that are not in the prior art, which would occur to persons skilled in the art upon reading the foregoing description. For example, whereas measuring blood pressure is described hereinabove with respect to many preferred embodiments of the present invention, for some other embodiments, other physiological parameters of the user may be measured, such as, for example, heart rate, blood oxygenation, or respiration.

Alternatively or additionally, while some preferred embodiments are described hereinabove with respect to driving modifications of the user's blood pressure or heart rate, in a preferred embodiment of the present invention, the rate, magnitude, and/or another aspect of peristalsis is modified through the effects of music or another intervention as described hereinabove, mutatis mutandis. For this embodiment, sensor (e.g., electrical or acoustic sensors) are preferably coupled to a site in a vicinity of the user's gastrointestinal tract, so as to detect aspects of the peristalsis and to enable the processor to optimize the applied intervention. Typically, but not necessarily, this embodiment employs methods and apparatus described in the above-cited U.S. Pat. No. 5,690,691 to Chen, et al. and/or in the above-cited article by Gimondo and Mirk.

In addition, while many of the embodiments are described as generating music or another output signal which guides the user to intentionally modify an aspect of a voluntary action (e.g., breathing), for some applications, the user semi-consciously or unconsciously modifies the action. For example, as described hereinabove, many people unconsciously and effortlessly entrain their breathing, walking, or running to an outside rhythmic stimulus, such as strongly-rhythmic music or even a blinking light. Similarly, some of these embodiments of the present invention may be applied to people who are not consciously attempting to coordinate the voluntary action with the rhythm of the applied intervention. Thus, for some applications, a user of some of these embodiments may read, talk, eat, or even sleep, while one or more sensors are measuring respective physiological variables of the user, and an intervention such as is described herein is applied to the user.

It is also to be understood that whereas many embodiments of the present invention are described hereinabove with respect to treating a user's hypertension, the scope of the present invention includes applying an intervention (e.g., modifying the user's respiration) so as to treat hypotension or other blood pressure disorders.

The invention claimed is:

1. Apparatus for measuring mechanical deformation, comprising:
   a housing;
   a base electrode;
   a deformable electrode, mechanically coupled to the base electrode and to the housing, the base electrode and the deformable electrode defining a capacitor having capacitance, such that the capacitance is varied responsive to deformation of the deformable electrode; and
   at least one deformable-electrode supporter,
   wherein when no force is applied to the deformable electrode, a shortest distance between the base electrode and the deformable electrode varies along a length of the deformable electrode, the base electrode and the deformable electrode converging, at a fixed-region along the length of the base electrode, to a closest possible distance from each other, which is fixed by structure of the apparatus, and
   wherein the deformable-electrode supporter is configured to support the deformable electrode at a support region that is remote from the fixed region.

2. Apparatus according to claim 1, wherein the deformable electrode is adapted to be coupled to a user, such that the deformation is responsive to respiration of user.

3. Apparatus according to claim 1, and further comprising a member, mechanically coupled to the deformable electrode, such that movement of the member deforms the deformable electrode and varies the capacitance.

4. Apparatus according to claim 3, and further comprising a belt, adapted to be placed around a torso of a user and to cause movement of the member responsive to a change in circumference of the torso.

5. Apparatus according to claim 3, wherein the member is adapted to be in physical contact with the deformable electrode.

6. A method for measuring mechanical deformation with apparatus, comprising mechanically coupling a base electrode to a deformable electrode, the base electrode and the deformable electrode defining a capacitor having capacitance, such that:
   the capacitance is varied responsive to deformation of the deformable electrode,
   when no force is applied to the deformable electrode, a shortest distance between the base electrode and the deformable electrode varies along a length of the deformable electrode, the base electrode and the deformable electrode converging, at a fixed-region along the length of the base electrode, to a closest possible distance from each other, which is fixed by structure of the apparatus, and
   the deformable electrode is supported by a deformable electrode supporter at a support region that is remote from the fixed region.

* * * * *